(12) United States Patent
Criscione et al.

(10) Patent No.: US 7,871,366 B2
(45) Date of Patent: Jan. 18, 2011

(54) DEVICE FOR THE MODULATION OF CARDIAC END DIASTOLIC VOLUME

(75) Inventors: John C. Criscione, College Station, TX (US); Saurabh Biswas, Bryan, TX (US); Stan Hall, Colleyville, TX (US); Lewis Harrison, Arlington, TX (US); Dennis Robbins, Richardson, TX (US)

(73) Assignees: The Texas A&M University System, College Station, TX (US); Corinnova Incorporated, Houston, TX (US)

( * ) Notice: Subject to any disclaimer, the term of this patent is extended or adjusted under 35 U.S.C. 154(b) by 654 days.

(21) Appl. No.: 11/830,488

(22) Filed: Jul. 30, 2007

(65) Prior Publication Data

US 2008/0021260 A1      Jan. 24, 2008

Related U.S. Application Data

(63) Continuation-in-part of application No. 11/400,148, filed on Apr. 6, 2006.

(60) Provisional application No. 60/668,640, filed on Apr. 6, 2005.

(51) Int. Cl.
  *A61N 1/362*   (2006.01)
  *A61M 1/12*    (2006.01)
(52) U.S. Cl. .................................................. 600/16
(58) Field of Classification Search ................ 600/3, 600/16, 17, 37; 623/3.1
See application file for complete search history.

(56) References Cited

U.S. PATENT DOCUMENTS

| | | | |
|---|---|---|---|
| 2,826,193 A | 3/1958 | Vineberg | |
| 3,034,501 A | 5/1962 | Hewson | |
| 3,233,607 A | 2/1966 | Bolie | |
| 3,513,836 A | 5/1970 | Sausse | |

(Continued)

FOREIGN PATENT DOCUMENTS

WO      99/22784      5/1999

(Continued)

OTHER PUBLICATIONS

Anstadt, M.P., et al., "Non-blood contacting biventricular support for severe heart failure." Ann Thorac Surg (2002), 73:556-62.

(Continued)

*Primary Examiner*—Carl H Layno
*Assistant Examiner*—Brian T Gedeon
(74) *Attorney, Agent, or Firm*—Chalker Flores, LLP; Chainey P. Singleton; Edwin S. Flores

(57) ABSTRACT

The present invention provides methods, systems, kits and devices that reduce dyskinesis and hypokinesis. For example, the direct compression cardiac device may be positioned about at least a portion of a heart, and includes a resilient inner panel in contact with at least a portion of the heart periphery, one or more resilient members positioned about the resilient inner panel and at least partially surrounded by an expandable outer panel. The resistance supplied by the inner panel to the heart may be modulated to control the end-diastolic heart volume and remodel the heart, the resistance supplied by the expandable outer panel to the heart may be modulated to control the end-systolic heart volume and remodel the heart or both.

26 Claims, 29 Drawing Sheets

U.S. PATENT DOCUMENTS

| | | | |
|---|---|---|---|
| 4,048,990 A * | 9/1977 | Goetz | 601/153 |
| 4,536,893 A | 8/1985 | Parravicini | |
| 5,119,804 A | 6/1992 | Anstadt | |
| 5,256,132 A | 10/1993 | Snyders | |
| 5,749,839 A | 5/1998 | Kovacs | |
| 5,863,574 A | 1/1999 | Julien | |
| 6,224,540 B1 | 5/2001 | Lederman et al. | |
| 6,387,042 B1 | 5/2002 | Herrero | |
| 6,540,666 B1 | 4/2003 | Chekanov | |
| 6,592,619 B2 | 7/2003 | Melvin | |
| 6,595,912 B2 | 7/2003 | Lau et al. | |
| 6,602,182 B1 | 8/2003 | Milbocker | |
| 6,602,184 B2 | 8/2003 | Lau et al. | |
| 6,612,978 B2 | 9/2003 | Lau et al. | |
| 6,612,979 B2 | 9/2003 | Lau et al. | |
| 6,663,558 B2 | 12/2003 | Lau et al. | |
| 6,784,283 B2 | 8/2004 | Anderson et al. | |
| 7,445,593 B2 * | 11/2008 | Criscione | 600/16 |
| 7,494,459 B2 * | 2/2009 | Anstadt et al. | 600/17 |
| 2002/0065449 A1 * | 5/2002 | Wardle | 600/37 |
| 2007/0260108 A1 | 11/2007 | Criscione | |

OTHER PUBLICATIONS

Artrip, J.H., et al., "Physiological and hemodynamic evaluation of nonuniform direct cardiac compression." Circulation (1999), 100(suppl II):236-43.

Cohn, J. N., "Cardiac Remodeling-Concepts and Clinical Implications: A Consensus Paper from an International Forum on Cardiac Remodeling," Journal of American College of Cardiology (2000), 35(3):569-582.

Dipla, K., et al., "Myocyte recovery after mechanical circulatory support in humans with end-stage heart failure." Circulation (1998), 97:2316-2322.

Goldstein, D.J., et al., "Medical progress: implantable left ventricular assist devices." N Engl J Med (1998), 339 (21):1522-1533.

Heerdt, P.M., et al., "Chronic unloading by left ventricular assist device reverses contractile dysfunction and alters gene expression in end-stage heart failure." Circulation (2000), 102:2713-2719.

Karvarana, M.N., et al., "Circulatory support with a direct cardiac compression device: a less invasive approach with the AbioBooster device." J Thorac Cardiovasc Surg (2001), 122:786-787.

Kawaguchi, O., et al., "Mechanical enhancement of myocardial oxygen saving by synchronized dynamic left ventricular compression." J Thorac Cardiovasc Surg (1992), 103:573-81 (Abstract).

Kherani, A.R., et al., "Ventricular assist devices as a bridge to transplant or recovery." Cardiol (2004), 101:93-103.

Omens, J.H. "Stress and strain as regulators of myocardial growth." Prog. Biophys. Molec. Biol. (1998), 69:559-572.

Oz, M.C., et al., "Direct cardiac compression devices." J Heart Lung Transplant (2002), 21:1049-1055.

Rose, E.A., et al., "Long-term use of left ventricular assist device for end-stage heart failure." N Engl J Med (2001), 345(20):1435-1443.

Williams, M.R., and Artrip, J.H. "Direct cardiac compression for cardiogenic shock with the CardioSupport System." Ann Thorac Surg (2001), 71:S188-9.

International Search Report and Written Opinion for PCT/US2008/071618 dated Feb. 12, 2009.

* cited by examiner

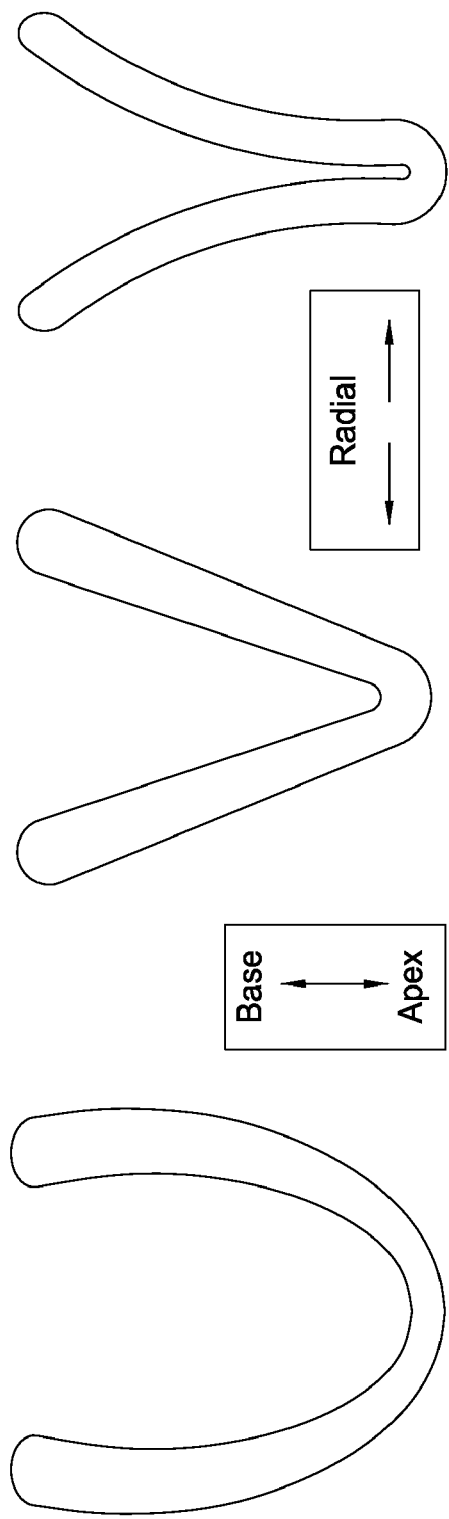
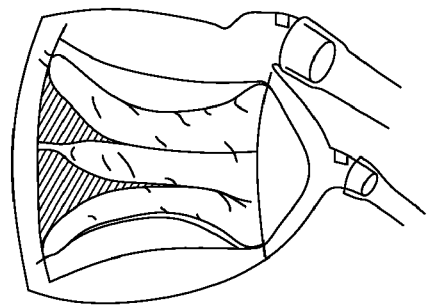
FIG. 2A  FIG. 2B  FIG. 2C  FIG. 2D

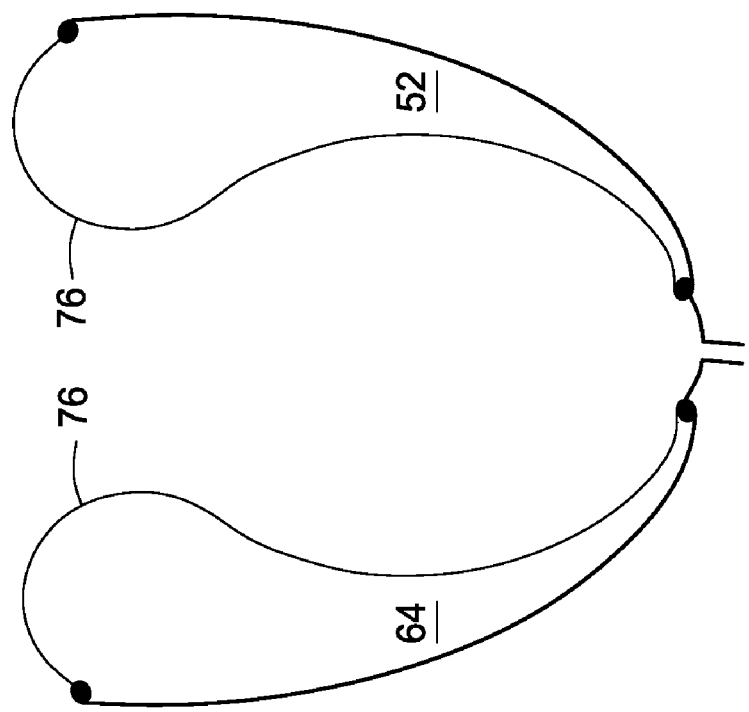
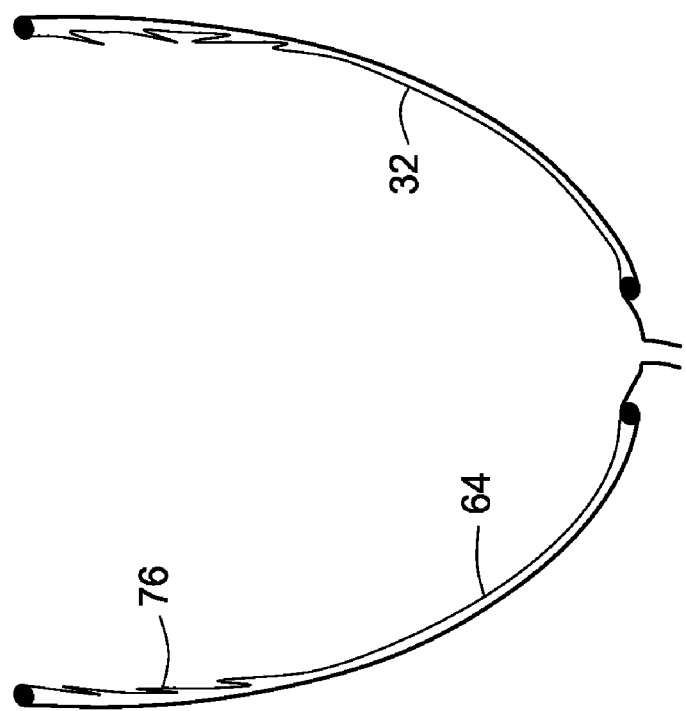

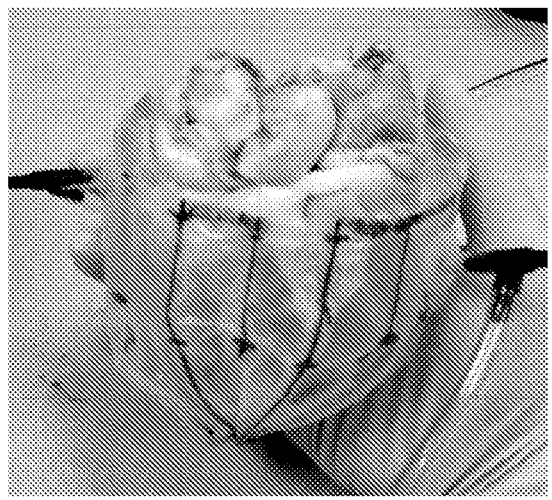
FIG. 14
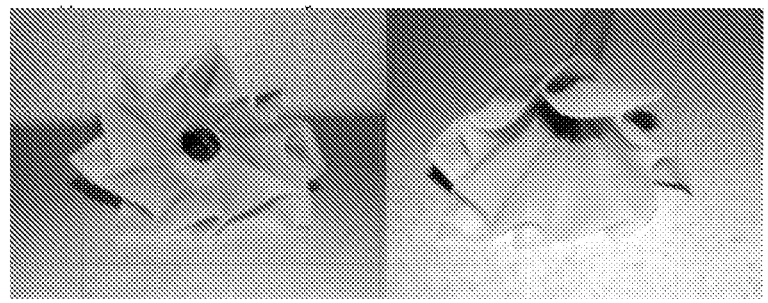
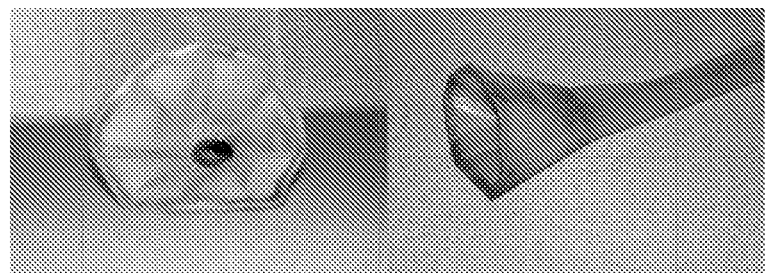
FIG. 15

DEVICE FOR THE MODULATION OF CARDIAC END DIASTOLIC VOLUME

CROSS-REFERENCE TO RELATED APPLICATIONS

This application is a continuation-in-part and claims priority based on U.S. patent application Ser. No. 11/400,148, filed Apr. 6, 2006, which claims priority to U.S. Provisional Application Ser. No. 60/668,640, filed Apr. 6, 2005, and is related to U.S. patent application Ser. No. 10/870,619, filed Jun. 17, 2004, the contents of each is incorporated by reference herein in its entireties.

STATEMENT OF FEDERALLY FUNDED RESEARCH

This invention was made with U.S. Government support under Contract No. 4R42HL080759-02 awarded by the NIH. The government has certain rights in this invention.

TECHNICAL FIELD OF THE INVENTION

The present invention relates in general to a mechanical interface for the heart of a patient to improve its pumping function, and, more particularly, modulate contraction strain patterns on a diseased or damaged heart in order to reduce dyskinetic or hypokinetic motions.

BACKGROUND OF THE INVENTION

Congestive heart failure affects an estimated 5 million people and results in an estimated $28.8 billion dollars being spent on health care relating to congestive heart failure (see AHA, 2003). As a result congestive heart failure treatments have become a substantial research interest.

There are numerous cardiac devices, artificial hearts and heart assist devices currently on the market. In addition, other therapies like drugs, biventricular pacing, stem cell therapies, blood contacting assist devices, surgical manipulations, or passive stents and constraints typically off-load the heart and thus only modulate the strain pattern indirectly (e.g., through greater ejection fraction).

Pharmacotherapy is minimally invasive and is a preferred form of treatment for congestive heart failure; however, pharmacotherapy has risks. Additionally, pharmacotherapy can be ineffective for mechanical problems, such that surgical intervention is necessary. For example, cardiovascular diseases with aberrant growth and remodeling may be in the class of diseases with a mechanical etiology, because it is now evident that local mechanical stimuli are major controllers of growth and remodeling in cardiovascular tissues. As the heart functions to produce mechanical work, mechanical strain may be one of the primary stimuli in cardiac development and adaptation.

For example, a recent publication (Rose et al., 2001) examined the Randomized Evaluation of Mechanical Assistance for the Treatment ("REMATCH trial") of congestive heart failure ("CHF"). The REMATCH trial was a major, multicenter (20), large trial (129 patients) designed to compare long-term cardiac assist treatments to pharmacological treatment in the areas of survival, serious adverse events, number of days of hospitalization and quality of life. The REMATCH trial states, "Patients with mild-to-moderate heart failure [SOLVD, 1991] and, recently, some with more severe disease [Packer et al., 2001] have been shown to benefit from drug therapy. Nevertheless, the survival and the quality of life of patients with severe heart failure remain limited. Cardiac transplantation is the only treatment that provides substantial individual benefit, but with fewer than 3,000 donor hearts available worldwide per year, its impact is epidemiologically trivial [Hosenpud et al., 2000]."

Despite having an increased number of adverse events and hospitalizations, the group with mechanical assist had a significantly higher survival rate and quality of life. The success of the REMATCH trial contributed to the recent action of the FDA to approve cardiac assist devices for use in end-stage heart failure patients who are not waiting for a transplant. Prior to this, cardiac assist devices were only approved as a bridge to transplantation.

One heart assist device is shown in U.S. Pat. No. 5,119,804, issued on Jun. 9, 1992 to Anstadt, for a cardiac massage apparatus and a drive system. The cardiac massage apparatus includes a cup having a liner that is connected within the cup at its upper and lower ends. Dimensions defining an optimum cup shape as a function of ventricular length are disclosed wherein the heart remains within the cup when mechanically activated.

Other examples include U.S. Pat. Nos. 6,663,558; 6,612,979; 6,612,978; 6,602,184 and 6,595,912 issued to Lau, et al., for a cardiac harness to treat congestive heart failure. The harness applies elastic, compressive reinforcement on the left ventricle to reduce deleterious wall tension and to resist shape change of the ventricle during the mechanical cardiac cycle. Rather than imposing a dimension beyond which the heart cannot expand, the harness provides no hard limit over the range of diastolic expansion of the ventricle. Instead, the harness follows the contour of the heart throughout diastole and continuously exerts gentle resistance to stretch.

U.S. Pat. No. 6,602,182, issued Aug. 5, 2003 to Milbocker, for a unified, non-blood contacting, implantable heart assist system surrounds the natural heart and provides circumferential contraction in synchrony with the heart's natural contractions. The pumping unit includes adjacent tube pairs arranged along a bias with respect to the axis of the heart and bound in a non-distensible sheath forming a heart wrap. The tube pairs are tapered at both ends such that when they are juxtaposed and deflated they approximately follow the surface of the diastolic myocardium. Inflation of the tube pairs causes the wrap to follow the motion of the myocardial surface during systole. A muscle-driven or electromagnetically powered energy converter inflates the tubes using hydraulic fluid pressure. An implanted electronic controller detects electrical activity in the natural heart, synchronizes pumping activity with this signal, and measures and diagnoses system as well as physiological operating parameters for automated operation. A transcutaneous energy transmission and telemetry subsystem allows the Unified System to be controlled and powered externally.

U.S. Pat. No. 6,592,619, issued on Jul. 15, 2003 to Melvin, for an actuation system for assisting the operation of the natural heart. The system includes a framework for interfacing with a natural heart, through the wall of the heart, which includes an internal framework element configured to be positioned within the interior volume of a heart and an external framework element configured to be positioned proximate an exterior surface of the heart. The internal framework is flexibly suspended with respect to the external frame. An actuator system is coupled to the framework and configured to engage an exterior surface of the heart. The actuator system includes an actuator band extending along a portion of a heart wall exterior surface. The actuator band is selectively movable between an actuated state and a relaxed state and is operable, when in the actuated state, to assume a predetermined shape and thereby indent a portion of the heart wall to affect a reduction in the volume of the heart. A drive apparatus is coupled to the actuator band and is operable for selectively moving the actuator band between the relaxed and actuated states to achieve the desired assistance of the natural heart.

U.S. Pat. No. 6,224,540 issued on May 1, 2001 to Lederman, et al., relates to a passive girdle for heart ventricle for therapeutic aid to patients having ventricular dilatation. A passive girdle is wrapped around a heart muscle which has dilatation of a ventricle to conform to the size and shape of the heart and to constrain the dilatation during diastole. The girdle is formed of a material and structure that does not expand away from the heart but may, over an extended period of time be decreased in size as dilatation decreases.

Other heart assist devices include direct cardiac compression devices; however, these devices were designed to enhance the ejection motion of the heart or designed for ease of implantation and therefore, introduce aberrant strain patterns during contraction. For example, passive direct compression cardiac devices (e.g., HeartNet (Paracor Surgical Inc.) and C or Cap (Acorn cardiovascular Inc.)) are made of biocompatible mesh or nitinol and placed around the heart as an elastic, compressive reinforcement on the left ventricle to reduce deleterious wall tension during diastole (i.e., restrict end diastolic volume) and to resist shape change of the ventricle during the mechanical cardiac cycle. Similarly, active direct cardiac compression devices are also used to help in ejection of the blood from the left ventricle, thus effectively offload the heart and does not directly modulate the strain pattern, e.g., the rigid cup shaped device of Myo Vad (Myotech LLC). A major disadvantage of this device is that the process of the ejection of the blood inverts the curvature of the heart, which induces aberrant motion and hence an aberrant strain pattern. The inverted curvature leads to a flawed ventricular wall contour and results in regions of stress concentrations in the ventricle, which might lead to aneurysm formation, fibrosis, and impairment of the contractility and compliance of the ventricle. The resulting irregular contour of the endocardial surface of the left ventricle may lead to localized hemostasis or turbulence, which may in turn lead to thrombus formation and possible thromboembolism.

The foregoing problems have been recognized for many years and while numerous solutions have been proposed, none of them adequately address all of the problems.

SUMMARY OF THE INVENTION

The present inventors recognized that direct cardiac compression devices can directly induce a particular geometry and strain pattern. The present invention provides a device to modulate the end-diastolic volume of the heart to benefit patients with cardiac conditions such as, for example, acute myocardial infarction (AMI) or dilated cardiomyopathy (DCM).

The present inventors recognized that strain is a primary controller of myocardial growth, remodeling, and recovery. The present inventors also recognized pharmacotherapy does not directly eliminate aberrant motion, yet drugs may restore motion indirectly through such mechanisms as afterload reduction. The present inventors recognized that a device, a system, a method and a kit are needed that eliminate aberrant strain patterns and once normal cardiac kinematics are restored the heart may be weaned from the device.

The present invention provides an implantable direct cardiac compression device that is collapsible for insertion through a small incision and that assumes the shape of the left ventricle keeping and actively modulates the strain pattern during contraction to eliminate aberrant motions (i.e., dyskinesis and hypokinesis). In addition, the present invention provides a control of stimuli that guide growth and remodeling the heart and reduce or eliminate abnormal growth or abnormal remodeling of the heart. The present invention also eliminates dyskinesis in the borderzone, for example, should preserve myocardium and thus minimize infarct expansion and secondary sequelli like cardiogenic shock, ventricular rupture and congestive heart failure. The present invention also modulates end diastolic volume and reduces deleterious wall tension during diastole. Furthermore, the present invention can be implanted in a minimally invasive manner under fluoroscopic guidance and is MRI compatible enabling monitoring of device and cardiac functionality.

The present invention relates to an inflatable end-systolic heart shaped bladder and methods of implanting, using and removing such a device. The present invention provides a contoured heart assist device that reduces dyskinesis and hypokinesis. The device includes a selectively inflatable end-systolic heart shaped bladder with one or more contoured supports configured to surround at least a portion of the heart to provide curvatures similar to the proper shape of the heart when pressurized. One or more fluid connections are in communication with the selectively inflatable end-systolic heart shaped bladder for pressurization and depressurization.

The present invention also provides a contoured direct cardiac compression device that applies forces to the exterior epicardial boundary of the heart to restrict inflow and modulate right flow versus left flow through the heart. The contoured direct cardiac compression device includes a selectively inflatable end-diastolic contoured bladder, an inlet connection and an outlet connection. The selectively inflatable end-diastolic contoured bladder includes one or more contoured supports, configured to engage releasably the heart. The one or more contoured supports protrude inward towards the right ventricle to decrease the end-diastolic volume of the right ventricle during diastole.

The present invention provides a method for promoting growth and remodeling the heart. A selectively inflatable end-systolic heart shaped bladder is positioned about at least a portion of the periphery of the heart of a patient. A fluid source that is connected to the selectively inflatable end-systolic heart shaped bladder, that inflates with a positive pressure during systole and deflates the selectively inflatable end-systolic heart shaped bladder during diastole is activated.

The present invention also provides a direct cardiac compression device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

The present invention provides a direct cardiac compression device that applies forces to the exterior epicardial boundary of the heart and is optimized to fit an end-systolic shaped heart geometry. The device includes 2 or more contoured compartments, an inlet connection and an outlet connection. The 2 or more contoured compartments are configured to surround at least a portion of the heart and individually contoured to provide curvatures that are similar to the proper end-systolic shape of the heart when pressurized. The inlet connection is in communication with the 2 or more inflatable contoured compartments and an outlet connection in communication with the 2 or more inflatable contoured compartments.

The present invention also provides a method of reshaping the heart muscle of a patient by providing a direct cardiac compression device that compresses the heart during contraction without inverting or significantly perturbing the curvatures of the heart. A selectively inflatable end-systolic heart shaped bladder is positioned about at least a portion of the periphery of the heart once access is made to the heart of the patient. The next step is the connecting of a fluid source to the selectively inflatable end-systolic heart shaped bladder to inflate with a positive pressure during systole and deflate the selectively inflatable bladder during diastole.

The present invention relates to a collapsible direct cardiac compression device and methods of implanting, using and removing such a device. In one embodiment, the invention relates to a direct cardiac compression device that surrounds the heart and includes a collapsible and a compression mechanism. The compression mechanism is operable to actively promote a contraction strain pattern on a diseased or damaged myocardium that promotes beneficial growth and remodeling of the myocardium. More particularly, the contraction strain pattern may be characterized by non-inversion or lack of gross perturbation of the heart's curvature. The device may include a plurality of inflatable chambers.

In another embodiment, the invention relates to a direct cardiac compression device having a collapsible structure and a plurality of inflatable chambers. The device exerts a non curvature-inverting contraction strain pattern when used on a heart. The device may be used on a heart without requiring attachment to the valve plane or other suturing to the heart.

The inflatable chambers may be formed from two sheets of material sealed and connected at a plurality of locations to form the plurality of chambers. The inflatable chambers may be made of a biocompatible material such as polyethylene. The direct cardiac compression device may also include a plurality of stabilizing rods, members or stents. An apical hole may be formed by the apical tips of the inflatable chambers.

The direct cardiac compression device may inflate the chambers in any way practical, but in a particular embodiment, it has at least one pneumatic drive line operable to inflate at least one of the plurality of inflatable chambers. It may include other pneumatic drives operable to inflate separate chambers. In some embodiments, the device may be operable to provide differential pressure to the left ventricle and the right ventricle during diastole when used on a heart.

Yet another embodiment of the invention provides a method of assisting a diseased or damaged heart by providing a soft shell direct cardiac compression device to the heart that compresses the heart during contraction without inverting or significantly perturbing the curvatures of the heart. Such methods include several beneficial effects such as inducing ventricular recovery in the heart, promoting growth and remodeling of the myocardium, and preserving the myocardioum in a borderzone of a myocardial infarct.

The method may include implanting or removing the device through a small or minimal thoracotomy. Such implantation or removal, more specifically, may occur through a sub-xyphoid incision, small left thoracotomy and/or through a mediastinoscopy procedure. The device may be implanted without suturing to the heart. Additionally, the method may also include gradually decreasing compression of the heart to allow the heart to be weaned from the direct cardiac compression device as it recovers.

In some embodiments, the unpressurized device has a very low structural rigidity such that it can be inserted and implanted through a small, sub-xiphoid incision or mini left thoracotomy. Similarly, explantation is minimally invasive and/or done through an enlargement/combination of driveline tracks. The pressurized device takes on a systolic configuration with normal cardiac curvatures. The induction of this systolic shape proactively modulates the strain pattern and intrinsically draws the heart into the device allowing for minimal sewing or similar attachment to the ventricles or valve plane. Hence, valve plane geometry and thus function are unaltered and implantation is quick and may be performed without cardiopulmonary bypass.

Pneumatic separation of the chambers that abut the RV inflow tract may permit partial impeding of RV filling to compensate for increased RV ejection. Because systolic geometry is not grossly abnormal, the amount of assist may be graded and thus a heart can be gradually weaned from the proposed device. In case of device failure, the default to vacuum on the pneumatic drive lines makes the device floppy and less likely to impede heart function. Additionally, aortic balloon technology that has been in use for 30 years may be used to drive the device of the present invention.

For example, the present invention provides a method of individually modulating the heart volumes by positioning a direct compression cardiac device about at least a portion of a heart. The direct compression cardiac device includes a resilient inner panel in contact with at least a portion of the heart periphery and at least partially surrounded by an expandable outer panel. The resistance supplied by the inner panel to the heart can be modulated optionally to control the end-diastolic heart volume. The resistance supplied by the expandable outer panel to the heart can be modulated optionally to control the end-systolic heart volume. In addition, both can be modulated optionally.

The present invention provides a method of remodeling the shape of a heart of a patient by controlling the end-diastolic heart volume and the end-systolic heart volume. The method includes determining the shape of the heart of the patient and positioning a direct compression cardiac device about at least a portion of a heart. The direct compression cardiac device includes a resilient inner panel in contact with at least a portion of the heart periphery and at least partially surrounded by an expandable outer panel. Optionally, the resistance supplied by the inner panel to the heart may be modulated to control the end-diastolic heart volume and remodel the heart, the resistance supplied by the expandable outer panel to the heart to control the end-systolic heart volume and remodel the heart or both.

A direct cardiac compression heart assist device is also provided by the present invention. The device includes a resilient inner panel and an inflatable outer panel. The resilient inner panel is in contact with a heart periphery having two or more at least partially overlapped membranes with one or more resilient members and is contoured to provide curvatures generally in the shape of the heart. The resilient inner panel supplies resistance to the heart to affect the end-diastolic heart volume. The inflatable outer panel includes one or more inflatable membranes positioned at least partially around the resilient inner panel to inflate and deflate to provide resistance to the heart to affect the end-systolic heart volume. One or more fluid connections are in communication with the inflatable outer panel for inflation and deflation.

The present invention provides a method of individually modulating the end-diastolic heart volume and the end-systolic heart volume by positioning a direct compression cardiac device about at least a portion of the heart. The direct compression cardiac device includes a resilient inner panel in contact with the heart periphery and surrounded by an inflatable outer panel. The resilient inner panel includes two or more at least partially overlapped membranes having one or more resilient members and contoured generally to the shape of the heart. The inflatable outer panel includes one or more inflatable membranes in communication with one or more connections to selectively expand and compress the inflatable outer panel to provide resistance to the heart periphery. Optionally, the resistance supplied by the inner panel to the heart can be modulated to control the end-diastolic heart volume. Optionally, the resistance supplied by the expandable outer panel to the heart can be modulated to control the end-systolic heart volume. Furthermore, both the resistance supplied by the inner panel and the outer panel can be modulated.

For example, the present invention includes a direct cardiac compression heart assist device to affect the end-diastolic heart volume. The device includes a resilient panel with two or more at least partially overlapped membranes in contact with a heart periphery. The two or more at least partially overlapped membranes are contoured to accommodate generally the shape of the heart and include one or more resilient members that supply resistance to the heart to affect the end-diastolic heart volume.

The present invention provides a direct cardiac compression device that promotes a contraction strain pattern on a heart that reduces dyskinetic or hypokinetic motions. The device includes a resilient inner panel in contact with a heart periphery having about eight overlapped membranes contoured to accommodate generally the shape of the heart Each of the overlapped membranes having one or more resilient members. The resilient inner panel supplies resistance to the heart to affect the end-diastolic heart volume. An inflatable outer panel includes one or more inflatable membranes positioned at least partially around the resilient inner panel to inflate and deflate to provide resistance to the heart to affect the end-systolic heart volume. The inflatable outer panel also includes one or more fluid connections for inflation and deflation.

The present invention provides a method for delivering a direct cardiac compression heart assist device by creating a heart apex access site and contacting a heart periphery with a direct cardiac compression heart assist device contoured to provide curvatures generally in the shape of the heart comprising a resilient inner panel comprising two or more at least partially overlapped membranes having one or more resilient members and contoured to provide curvatures generally in the shape of the heart, wherein the resilient inner panel supplies resistance to the movement of the heart to affect the end-diastolic heart volume, an inflatable outer panel comprising one or more inflatable membranes positioned at least partially around the resilient inner panel to inflate to provide resistance to the movement of the heart to affect the end-systolic heart volume and one or more fluid connections in communication with the inflatable outer panel for inflation and deflation. The one or more fluid connection can then be connected to a fluid source. In addition, the direct cardiac compression heart assist device is connected to a delivery device for insertion into the heart apex access site.

The present invention also provides a method for delivering a direct cardiac compression heart assist device by creating a heart apex access site and providing a heart periphery with a direct cardiac compression heart assist device contoured to provide curvatures generally in the shape of the heart comprising a resilient inner panel comprising two or more at least partially overlapped membranes having one or more resilient members and contoured to provide curvatures generally in the shape of the heart, wherein the resilient inner panel supplies resistance to the movement of the heart to affect the end-diastolic heart volume, an inflatable outer panel comprising one or more inflatable membranes positioned at least partially around the resilient inner panel to inflate to provide resistance to the movement of the heart to affect the end-systolic heart volume and one or more fluid connections in communication with the inflatable outer panel for inflation and deflation. A direct cardiac compression heart assist delivery device is in communication with a direct cardiac compression heart assist device to aid in the positioning about the heart periphery. The direct cardiac compression heart assist delivery device is inserted through the heart apex access site and positioned about the periphery of the heart and the direct cardiac compression heart assist delivery device withdrawn from the heart apex access site.

To both implant and explant the assist devices of the present invention, a small thoracotomy is desirable. The unpressurized device has a very low structural rigidity and the soft outer shell allows implantation through a much smaller incision. The device has both diastolic and systolic configurations that produce normal cardiac curvatures.

BRIEF DESCRIPTION OF THE DRAWINGS

For a more complete understanding of the features and advantages of the present invention, reference is now made to the detailed description of the invention along with the accompanying figures and in which:

FIG. 2 is a diagram shows the normal, null and inverted curvature in apex-to-base, radial plane of the heart;

FIG. 6 is a schematic diagram of the cross-section of a device according to one embodiment of the present invention without a heart inside, wherein

FIG. 7 is a schematic diagram of the long-section of a device according to one embodiment of the present invention without a heart inside, wherein FIG. 7A is in the deflated state and FIG. 7B is in the pressurized state;

FIG. 8 is a schematic diagram of the cross-section of a device according to one embodiment of the present invention with a heart inside, wherein FIG. 8A is in the deflated state and FIG. 8B is in the pressurized state;

FIG. 9 is a schematic diagram of the long-section of a device according to an embodiment of the present invention with a heart inside, wherein FIG. 9A is in the deflated state and FIG. 9B is in the pressurized state;

FIG. 14 is an image that illustrates a device according to one embodiment of the present invention with an ovine heart inside;

FIG. 15 is an image that illustrates a device according to one embodiment of the present invention;

FIG. 21A is an image that illustrates a device having uninflated bladders, while

DETAILED DESCRIPTION OF THE INVENTION

Figure 1:
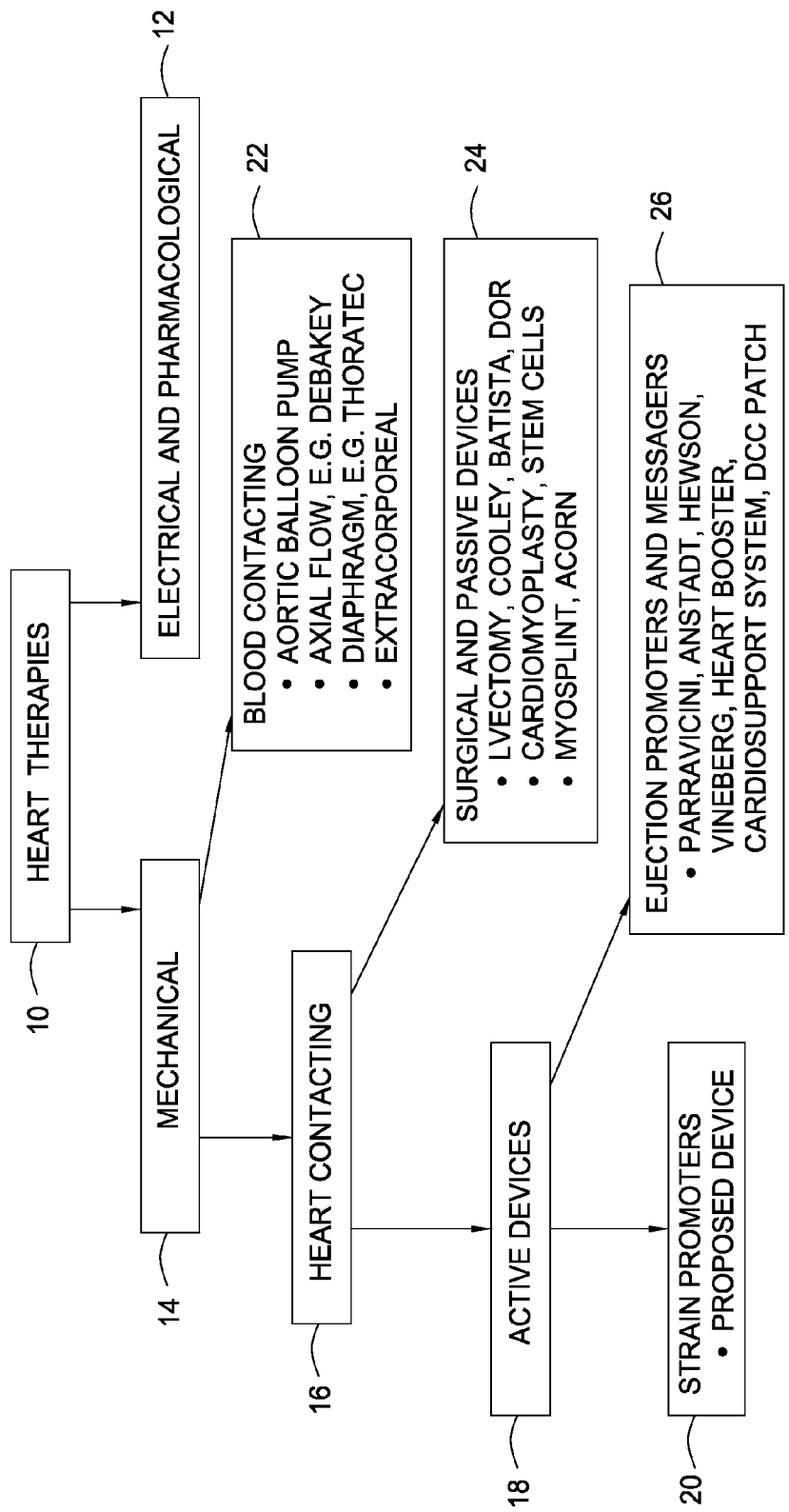
FIG. 1 is a chart that illustrates the classification of heart therapies.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the "cardiac rekinesis therapy" is the restoration of physiological or beneficial motion to the heart, or in other words, to eliminate aberrant or pathophysiological motions or strains, as opposed to circulatory assist therapies.

As used herein, a "biomedical material" is a material, which is physiologically inert to avoid rejection or other negative inflammatory response.

The present invention provides an implantable direct cardiac compression device with a collapsible structure that assumes the shape of the left ventricle keeping a inwardly directed pressure to prevent the enlargement of the ventricle and provides adjustment of the end diastolic volume for limiting/reducing the end systolic volume.

The present invention provides a contoured heart assist device that reduces dyskinesis and hypokinesis. The device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization.

The one or more contoured supports form one or more inflatable compartments having an expanded curvature optimized to fit generally the proper end-systolic shape of the heart. The selectively inflatable end-systolic heart shaped bladder includes an inner membrane that is at least partially folded when depressurized and at least partially unfolded when pressurized. In another embodiment, the selectively inflatable end-systolic heart shaped bladder includes an inner membrane that is at least partially folded when depressurized and at least partially unfolded when pressurized and an outer membrane that is at least partially folded when depressurized and at least partially unfolded when pressurized. Other embodiments may include various combinations thereof.

The one or more contoured supports may include one or more dividers individually of similar or different materials, one or more wires individually of similar or different materials or a combination thereof to form a shape generally appropriate to the proper end-systolic shape of the heart. The selectively inflatable end-systolic heart shaped bladder includes a material that is substantially biocompatible, fluid-impermeable and substantially elastic. For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof.

The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. That chambers distribution determination for a particular application and treatment is within the scope of the skilled artisan.

The inflatable tapered compartments are connected to a pneumatic pressure source through an inlet port and an outlet port. The device is inflated with a positive pressure during systole and deflated via suction during diastole. Although, other configurations and multiple connections are also possible depending on the particular application and configuration. The inlet port and an outlet port may be connected through a single connection for applying the positive pressure and the suction or negative pressure; alternatively, multiple connections may be used. In addition, the inlet port and an outlet port may be made anywhere about the boundary of the selectively inflatable end-systolic heart shaped bladder, e.g., near the base or near the apex.

The present invention also provides a contoured direct cardiac compression device that applies forces to the exterior, epicardial boundary of the heart to restrict inflow and modulate right flow versus left flow through the heart. The device includes a selectively inflatable end-diastolic contoured bladder having one or more contoured supports configured to releasable engage the heart. The one or more contoured supports protrude inward towards the right ventricle to decrease the end-diastolic volume of the right ventricle during diastole. The device also has an inlet connection and outlet connection in communication with the selectively inflatable end-diastolic contoured bladder to pressurize and depressurize the selectively inflatable end-diastolic contoured bladder. Residual pressure is applied about the right ventricle to not fully deflate during diastole.

Generally, the inlet line is in communication with the inlet connection to operatively expand the selectively inflatable end-diastolic contoured bladder and an outlet line is in communication with the outlet connection to operative withdraw fluid from the selectively inflatable end-diastolic contoured bladder. This allows connection to conventional devices to apply and remove pressure or custom devices specifically for the present invention.

The present invention provides a method for promoting growth and remodeling of the heart. Once access to the heart of the patient is provided, a selectively inflatable end-systolic heart shaped bladder can be positioned about at least a portion of the periphery of the heart.

The selectively inflatable end-systolic heart shaped bladder is then connected to a fluid source to inflate the selectively inflatable end-systolic heart shaped bladder with a positive pressure during systole and deflate the selectively inflatable end-systolic heart shaped bladder during diastole. Alternatively, the selectively inflatable end-systolic heart shaped bladder may be connected to the fluid source before positioning and subsequently activating to inflate and deflate the selectively inflatable end-systolic heart shaped bladder.

The present invention provides a contoured heart device that reduces dyskinesis and hypokinesis having an end-systolic heart contoured bladder with one or more contoured supports configured to surround at least a portion of the heart to provide curvatures that are similar to the proper end-systolic shape of the heart.

A method for promoting growth and remodeling of the heart is provided by the present invention. The method includes providing access to a heart of a patient and positioning a selectively inflatable end-diastolic heart shaped bladder about at least a portion of the periphery of the heart. The selectively inflatable end-diastolic heart shaped bladder is connected to a fluid source to the selectively inflatable end-diastolic heart shaped bladder to inflate with a positive pressure during systole and deflate the selectively inflatable bladder during diastole. The residual pressure is applied about the right ventricle to not fully deflate during diastole.

The selectively inflatable end-diastolic heart shaped bladder includes a pressurizable chamber formed by an inner membrane and an outer membrane and one or more contoured supports positioned within the pressurizable chamber to provide curvatures that are similar to the proper end-diastolic shape of the heart when the pressurizable chamber is pressurized. The one or more end-diastolic contoured supports form one or more inflatable compartments having an expanded curvature optimized to fit the heart geometry similar to the proper end-diastolic shape of the heart.

A direct cardiac compression device that applies forces to the exterior, epicardial boundary of the heart optimized to fit an end-systolic shaped heart geometry is provided by the present invention. The direct cardiac compression device includes a selectively inflatable bladder having one or more end-systolic contoured supports configured to surround at least a portion of the periphery of the heart and provide curvatures similar to the proper end-systolic shape of the heart when the pressurizable chamber is pressurized and one or more fluid connections in communication with the selectively inflatable bladder to pressurize and depressurize the selectively inflatable bladder.

The present invention also provides a direct cardiac compression device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

A method of assisting a diseased or damaged heart including providing a direct cardiac compression device that compresses the heart during contraction without inverting or significantly perturbing the curvatures of the heart by positioning a selectively inflatable end-systolic heart shaped bladder about at least a portion of periphery of the heart once access is made to the heart of the patient. The next step is the activating of a fluid source to the selectively inflatable end-systolic heart shaped bladder to inflate with a positive pressure during systole and deflate the selectively inflatable bladder during diastole.

The present invention provides a direct cardiac compression device that applies forces to the exterior, epicardial boundary of the heart optimized to fit an end-systolic shaped heart geometry. The device includes 1 or more contoured compartments, an inlet connection and an outlet connection. The 1 or more contoured compartments are configured to surround at least a portion of the heart and are individually contoured to provide curvatures that are similar to the proper end-systolic shape of the heart when pressurized. The inlet connection is in communication with the 1 or more inflatable contoured compartments and an outlet connection in communication with the 1 or more inflatable contoured compartments. For example, the present invention may be a direct cardiac compression device contoured to surround at least a portion of the heart. The device includes a single chamber with a plurality of structures contained therein that provide support to create the end-systolic shaped heart geometry.

The present invention also provides a dyskinesis and hypokinesis reduction system including a contoured heart assist device and a pressurization apparatus. The contoured heart assist device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization. The pressurization apparatus is in communication with the one or more fluid connections of the contoured heart assist device and includes a pressurization mechanism and a depressurization mechanism. The pressurization apparatus can apply pressure to the contoured heart assist device and remove pressure from the contoured heart assist device. The pressurization apparatus is controllable to allow for different cycling rates between pressurized and depressurized states.

The present invention relates to a direct cardiac compression device, particularly a soft-shelled direct cardiac compression device, and methods of implanting it. In particular it relates to a soft-shelled direct cardiac compression device that proactively modulates the strain pattern in the heart during contraction so as to reduce apoptosis in the myocardium and/or induce beneficial growth and remodeling of the myocardium and/or scarred regions. In particular, the device of the present invention does not invert or grossly perturb the curvature of the heart during contraction.

In some embodiments of the invention, the strain pattern is a physiological strain pattern, near physiologic strain pattern or a strain pattern that is not aberrant. A physiological strain pattern, for the purposes of the present invention, is one which does not invert or grossly alter the heart's curvature during systole. The invention may also maintain a normal curvature or strain pattern during diastole, or relaxation of the heart.

Using some embodiments of the present invention in a patient, for example to eliminate dyskinesis in the borderzone, preserves myocardium and minimizes infarct expansion and secondary complications, e.g., cardiogenic shock, ventricular rupture and CHF.

Many devices of the present invention may be inserted through a small incision. Many devices may also be attached to the atrial appendages via clamps that may also be used to synchronize the device to the electrocardiogram (ECG) or to pace the heart relative to the device activation.

Abnormal Strain Pattern. Cardiac strain patterns appear to be a major controller of myocardial growth, remodeling, and recovery. The exact normal or physiologic strain pattern of the heart is not currently known. Tests to determine the normal strain pattern in the heart of eight healthy sheep using bi-plane x-ray data of radio-opaque markers produced eight distinctly different patterns. It appears that cardiac contraction is similar to gait; there are gross similarities amongst individuals (e.g., toe off and hip twist), but the details can be distinctly different (e.g., angle of leg at toe off, amount and timing of the hip twist). In fact, we can often recognize people from their gait. It is difficult to describe a normal gait, yet it is quite easy to classify abnormal gaits. Likewise, normal cardiac strain pattern is difficult to define and prescribe, yet it is quite easy to identify abnormal cardiac strain patterns (e.g., dyskinesis and hypokinesis).

Thus, although some embodiments of the present invention may be able to produce a normal cardiac strain pattern, the same or other embodiments may also be able to eliminate or reduce abnormal strain patterns.

Importance of Strain in Ventricular Recovery. Ventricular recovery is needed and is possible. Fortunately, many researchers are addressing ventricular recovery with different approaches (e.g., surgical, drug, and gene therapy, stem cells and/or tissue engineering; see FIG. 1). However, it is well established that mechanical stimuli (e.g., stress or strain) are important epigenetic factors in cardiovascular development, adaptation, and disease (Taber, 2001; Humphrey, 2002). In the vasculature, for example, it appears that perturbed loading conditions heighten the turnover of cells (proliferation and apoptosis) and matrix (synthesis and degradation) in altered configurations, thus resulting in altered geometries, properties, and biologic function (Humphrey and Rajagopal, 2003). Just as similar mechanisms appear to be operative in hypertension, aneurysms, and micro-gravity induced changes, it is likely that they are operative in cardiac disease (Omens, 1998).

Congestive heart failure is compelling enough, yet dyskinesis or aberrant motion of the myocardium during contraction is likely important in all diseases of the heart that involve remodeling of the myocardium. Clearly, borderzone myocardium is viable (Bax et al., 2001) yet overloaded to the extent that it is dyskinetic, i.e., lengthens when it should shorten. It is likely that overloading leads to aberrant remodeling because (see review by Kherani et al., 2004) offloading leads to: normalization of genes that regulate calcium handling (Heerdt, et al., 2000), tumor necrosis factor (Torre-Amione et al., 1999) and cytoskeleton proteins (Wolff, et al., 1996); regression of fibrosis and cellular hypertrophy (Bruckner et al., 2001, Zafeiridis et al., 1998), and improved in-vitro contractile function (Dipla et al., 1998). Too much offloading is suspected to result in heart atrophy (Kherani, et al., 2004), whereby gradual weaning from a device should be sought along with combination therapy such as with clenbuterol (Hons et al., 2003).

Cellular and subcellular investigations have established that altered hemodynamic loading leads to growth and remodeling of myocytes and extra-cellular matrix (Grossman, 1980; Cooper, 1987; Weber et al., 1993; and Gerdes and Capasso, 1995) and myocytes are very sensitive to perturbations in strain and respond with altered gene expression (Komuro and Yazaki, 1993; Sadoshima and Izumo, 1997). Abnormal cardiac kinematics is often considered as a symptom of heart failure when in actuality it may be a primary cause of the aberrant growth and remodeling. By eliminating aberrant strain patterns with a device such as that of the present invention, it is possible that the growth and remodeling will stop being abnormal and start being restorative. Eliminating hypokinesis, for example, may reduce apoptosis, enhance myocyte development from native stem cells, and lead to ventricular recovery. Other congestive heart failure mechanisms or co-contributors are, among others, loss of myocyte shortening capability (Figueredo et al., 1994; Marian et al., 1997), calcium dysregulation (Feldman et al., 1993; Gwathmey et al., 1987), and unspecified myocyte apoptosis (Sabbah et al., 1998; Kajstura et al., 1995).

Artificial Hearts and Heart Assist Devices. There are numerous histories of artificial hearts and heart assist devices (Cooley and Frazier, 2000; Helman and Rose, 2000; Goldstein et al. 1998). FIG. 1 is a table that illustrates the various therapies that can be used. The various heart therapies 10 can be divided into electrical and pharmacological therapies 12 and mechanical therapies 14. The mechanical therapies 14 may be further divided into and include heart contracting therapies 16, which includes active devices 18. The active devices 18 include strain promoter devices 20. The mechanical therapies 14 commonly include blood contacting therapies 22, e.g., aortic balloon pump, axial flow, diaphragm and extracorporeal devices and therapies. The heart contracting therapies 16 commonly include surgical and passive devices 24, e.g., Left vectomy, cooley procedure, batista procedure, cardiomyoplasty, stem cell treatments and myosplint treatments. The active devices 18 include strain promoter devices 20 and ejection promoters and massagers 24. The ejection promoters and massagers 24 include parravicini treatment, anstadt treatment, hewson treatment, vineberg treatment, heart booster, cardiosupport system, DCC patch and so forth. The strain promoter device 20 includes the present invention. The various therapies in FIG. 1 (i.e., drugs, biventricular pacing, stem cell therapies, blood contacting assist devices, surgical manipulations, or passive stents and constraints etc.) typically off-load the heart and thus only modulate the strain pattern indirectly (e.g., through greater ejection fraction). Only direct cardiac compression devices (DCCDs) can directly induce a particular strain pattern. However, most prior DCCDs have been developed for enhancing ejection fraction or for ease of implantation rather than for strain modulation. Most induce aberrant strain patterns during contraction.

Cardiomyoplasty is a form of direct cardiac compression wherein a patient's own skeletal muscle is wrapped around the heart and stimulated during systole. Yet, the complications for cardiomyoplasty are significant: high peri-operative mortality and lengthy conditioning period (Oz et al., 2002). Similar to the recent special issue of Cardiology (2004, Volume 101, No. 1-3, Surgical Options for the Management of Congestive Heart Failure), cardiomyoplasty is considered in FIG. 1 as a surgical reconstruction as opposed to a method of cardiac assist.

Figure 9:
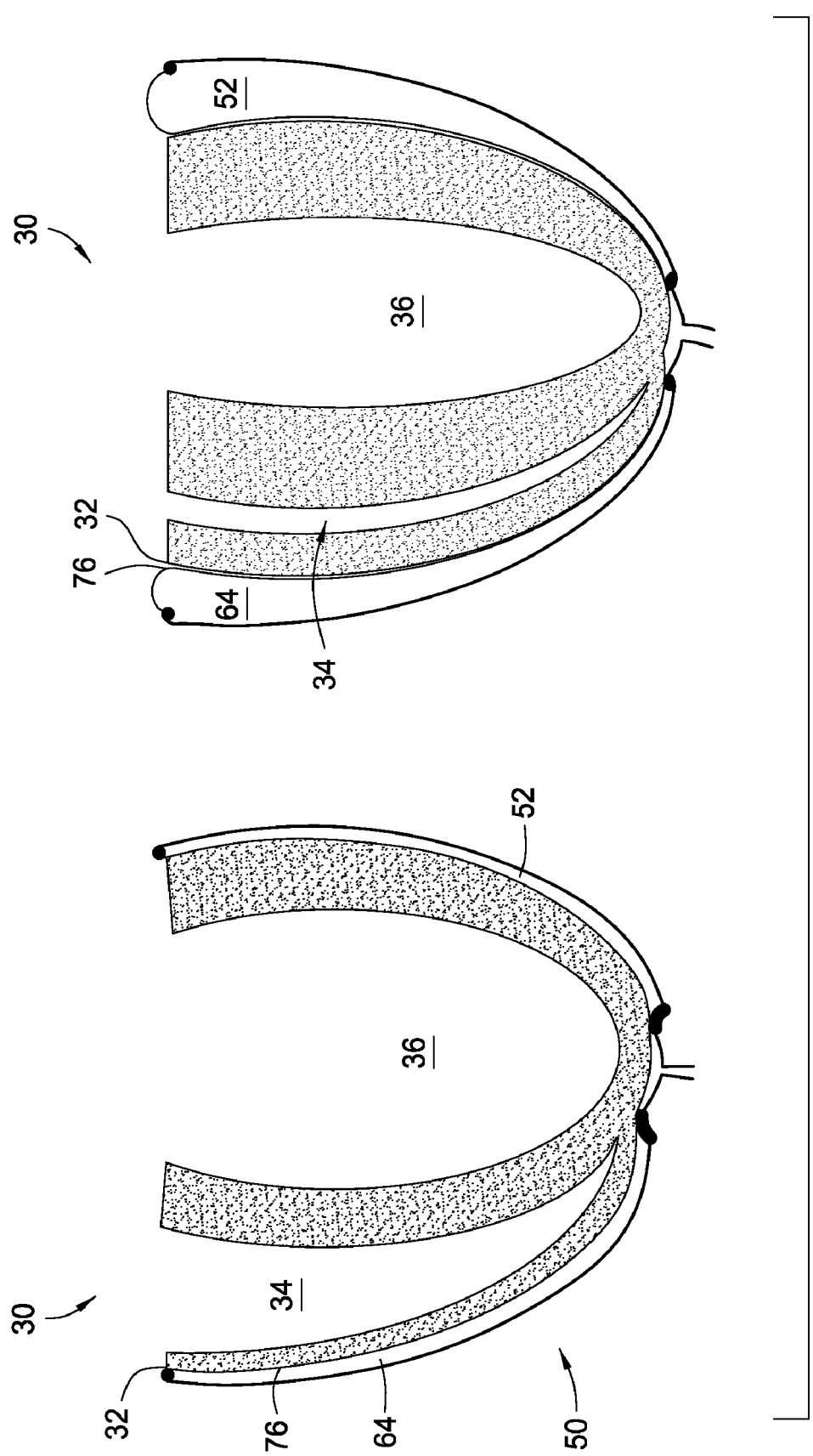

FIGS. 2A-2D shows the normal, null, and inverted curvature in apex-to-base, radial plane (long axis) of the heart. FIG. 2A illustrates a normal or positive curve with the inside of the curve toward the chamber, where the top references the base and the bottom references the apex. FIG. 2B illustrates a null curvature. FIG. 2C illustrates an inverted or negative curvature where the inside of the curve is away from the chamber. FIG. 2D is an illustration that shows the curvature inversion of the Anstadt cup as illustrated in FIG. 9 of U.S. Pat. No. 5,119,804. DCCDs have been characterized as most promising with good hemodynamics and ease of implantation (Karvarana et al., 2001; Anstadt et al., 2002; Oz et al., 2002). A number of DCCDs are being developed. The Anstadt cup is shown in FIG. 2 (Anstadt et al., 2002). The CardioSupport System by Cardio Technologies Inc. (Pine Brook, N.J.) is similar to the Anstadt cup. The attachment is via vacuum on the apical end and the assist is via inflation of a membrane that lies between a rigid shell and the epicardial surfaces of the right ventricle (RV) and left ventricle (LV) (Williams and Artrip, 2001). The devices of Parravicini (1985) and the Abio-Booster (Karvarana et al., 2001) by Abiomed Inc. (Danvers, Mass.) are sewn to the interventricular sulci, and elastic sacks between the shell and the epicardial surface are inflated during systole. The DCC Patch by Heart Assist Tech Pty Ltd (NSW, Australia) is similar to the AbioBooster. It is described in a news release of the Australian Technology Showcase as " . . . two patches shaped to suit the profile of the heart . . . inflated and deflated in synchrony with the heart . . . "

The heart booster (Kung et al., 1999) is composed of longitudinal tubes that have elliptical cross-sections with the major axis of the ellipse in the hoop direction. FIGS. 3A-3D shows the normal, increased, decreased, and inverted curvature in short axis sections of the heart as well as the inverted curvature produced by the existing Kung et al. device.

Figure 3B:
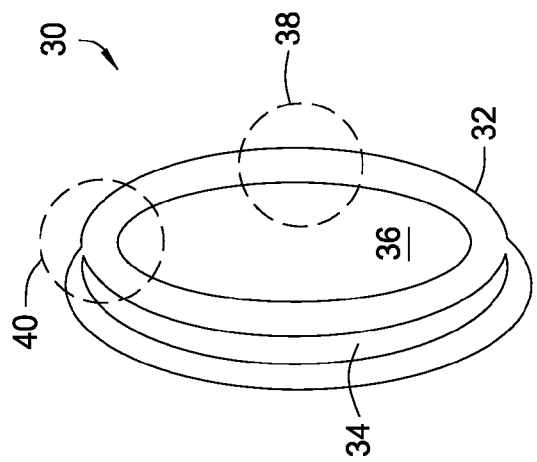
FIG. 3 is a schematic that illustrates the normal, increased, decreased and inverted curvature in short axis sections of the heart.
Figure 3D:
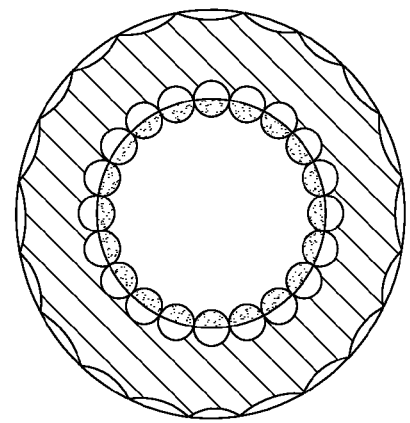
Figure 3A:
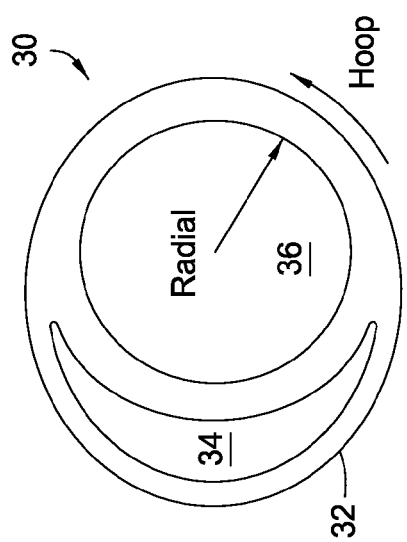
Figure 3C:
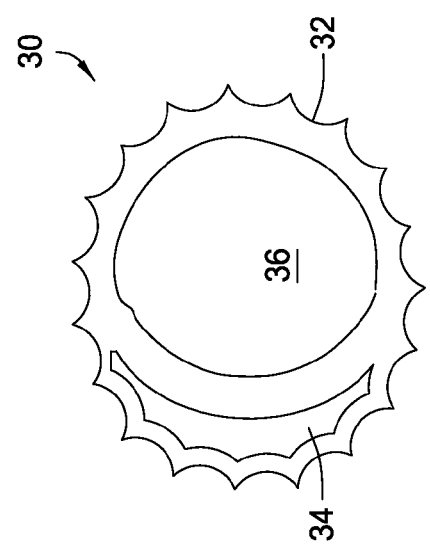

FIG. 3A illustrates the normal curvature of the heart 30 having an epicardium 32 and interior regions 34 and 36. The interior regions 34 and 36 have radii and curvatures that can be compared in different states. FIG. 3B illustrates the increased curvature of the heart 30 having the epicardium 32 and interior regions 34 and 36. The interior regions 34 and 36 for a radii and curvature that is different than FIG. 3A. The interior regions 34 and 36 show a decreased curvature region 38 and an increased curvature region 40. FIG. 3C illustrates a heart 30 having the epicardium 32 and interior regions 34 and 36 with an inverted or negative curvature on the epicardial boundary. The inverted or negative curvature on the epicardial boundary is illustrated by the scalloped shape of the epicardium 32. FIG. 3D illustrates the pressurized tube cross-sections of the device disclosed in Kung, et al. Early DCCDs were designed for heart massage during open chest procedures. They were not designed to be implanted because implant science was just beginning and advances in biomaterials and infection management had not yet occurred. The Vineberg (1958) and Hewson (1962) devices have bladders that inflate rhythmically inside a rigid shell.

To understand how all of these DCCDs induce aberrant strain patterns, it is extremely important to note that contraction strain depends on both the end-diastolic configuration (reference configuration) and the end-systolic configuration (current configuration). The strain field is a function of the gradient (with respect to reference position) of the mapping of material points from the reference configuration to the current configuration. Thus, the fact that prior DCCDs fit the diastolic configuration is inconsequential to achieving an appropriate contraction strain pattern because their end-systolic configurations are grossly aberrant. Although strains induced by such motions as torsion may not perturb the heart geometry; if the overall geometry is abnormal, then the strain must be abnormal. Unphysiological geometries are illustrated in FIGS. 2 and 3.

Generally, the curvature is inversely proportional to radius-of-curvature and that curvature changes sign when the origin of the radius-of-curvature changes sides. As should be evident from FIG. 2D, curvature inversion can greatly increase ejection fraction. However, the curvature of the ventricles in a normal heart does not invert during systole, thus rendering such motions grossly abnormal. A healthy heart, moreover, will resist having its curvature inverted and Artrip et al. (1999) shows that heart function needs to decline by 30% before the effect of "non-uniform direct cardiac compression" becomes noticeable. In short, the heart resists assist when a DCCD induces aberrant strains. DCCD devices described above induce motions that are grossly abnormal. The Vineberg device inverts curvature in long axis planes and short axis planes. The Anstadt cup and Cardio-Support System invert curvature in long axis planes yet preserve curvature in the short axis planes. The AbioBooster, DCC Patch, Hewson device, and Parravicini devices pull on the interventricular sulci and push on the freewall such that the curvature will increase at the sulci and decrease on the freewalls (see FIG. 3B). The Heart Booster inverts curvature in short axis planes, yet preserves curvature in the long axis planes. Because they were not designed to eliminate aberrant motions, it should not be surprising that these existing DCCDs described above induce aberrant strain patterns.

Additionally, none of the existing DCCDs described above are implanted in a minimally invasive fashion, and such an implantation method is highly desirable, clinically useful, and commercially advantageous. Given that strain is a primary stimulus of myocardial growth and remodeling, there is a need for a DCCD that eliminates dyskinetic or hypokinetic motions in the heart.

Figure 4A:
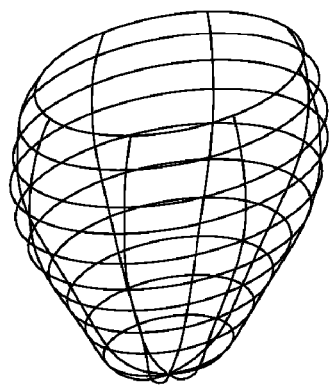
FIGS. 4A-4C are images that illustrate one embodiment of the heart device with a bovine heart inside.
Figure 4B:
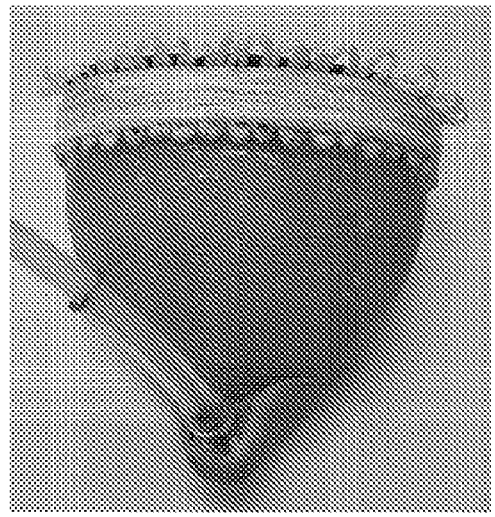
Figure 4C:
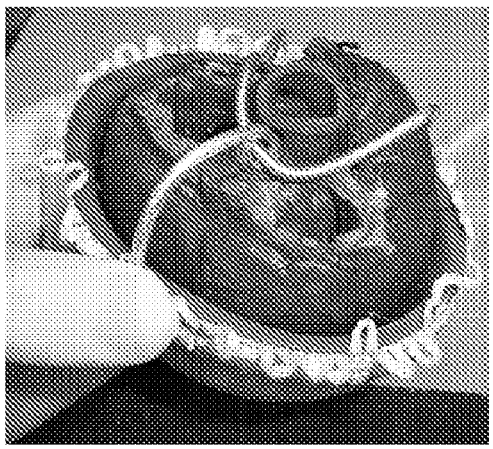

FIG. 4A shows a digital heart template determined from four ultrasound measurements. The template was used to produce the completed device seen in FIG. 4B and show in FIG. 4C attached to the heart of a young bovine. A prototype of a DCCD that proactively modulates the strain pattern during contraction has been constructed by Criscione et al. The prototype had a hard outer shell, and was implanted in a young bovine with pharmacologically induced heart failure (with esmolol hydrochloride, 7.5 mg/kg IV, as in Anstadt et al., 2002). Based on basic measurements (apex-base length, major and minor diameters, and distance from apex to equator) obtained from ultrasound, the device was constructed out of fiberglass, latex, brass, and nylon (FIG. 4). Because it was designed for acute experiments, there was no need for special manufacturing (i.e., removal of particulates and contaminates) or use of non-immunogenic materials (e.g., polyurethane and Ti).

This device, described in U.S. patent application Ser. No. 10/870,619, filed Jun. 17, 2004 (the '619 application), which is incorporated by reference herein, is the first implantable device to proactively modulate the strain pattern during contraction. The class of devices claimed in the '619 application are those that apply direct cardiac compression in a manner such that the end-diastolic and end-systolic configurations are physiologic with normal cardiac curvature, i.e. the class of direct cardiac compression device that achieve cardiac rekinesis therapy. The device disclosed in the '619 application must be attached to the valve plane of the heart. An attachment developed in benchtop trials consists of suture runs along the right and left free walls together with stents that go from the device shell to the center of the valve plane via the transverse pericardial sinus (anterior stent) and oblique pericardial sinus (posterior stent). In addition to keeping the heart in the device, the stents eliminate the need to suture near the coronary arteries in the interventricular sulci. The highly elastic membrane on the epicardial surface is sealed tightly with the rigid shell to contain the pneumatic driving fluid (e.g., air). A typical membrane requires about 1 kPa (10 cm $H_2O$) of vacuum to unimpede heart filling. This is similar to that of the native heart which typically requires about 9 cm $H_2O$ of transmural pressure to fill (e.g., 6 cm $H_2O$ of venous pressure minus a negative 3 cm $H_2O$ of intrathoracic pressure). The pressure waveforms (with compression for systole and tension for diastole) were generated by a Superpump System made by Vivitro Systems Inc. for cardiovascular research. The sync out signal was amplified, made bipolar, and used to pace the heart via right atriam (RA) leads.

One method of overcoming some negative effects of a hard-shelled DCCD (e.g., the need for a large thoracotomy) is to use a soft-shelled device. Soft-shelled devices include DCCDs with primary components that are constructed out of highly deformable materials. Such DCCDs can be collapsed and possibly implanted through a small incision this is likely to be sub-xiphoid (e.g., inferior to the xiphoid process) or a left thoracotomy. The Abiobooster and Heart Booster are currently existing soft-shelled devices. However, as described above, both of these devices induce an aberrant strain pattern in the heart. Additionally, implantation methods for these devices still require sewing the devices to the heart or pericardium.

It is evident that mechanical stimuli (e.g. stretching) induce altered gene expression in myocytes, and recent evidence suggests that such stimuli guide growth and remodeling of myocytes and ECM. Yet at first glance, heart failure should not occur if the myocardium uses mechanics to guide its growth to better meet the mechanical loads. However, upon assuming that there is a physiologic dynamic range (PDR) in which the growth and remodeling processes perform appropriately, it becomes evident that heart failure could be a classic type of instability, i.e., a unidirectional unchecked progression. Indeed, the insidious nature of congestive heart failure alone suggests that congestive heart failure is unstable growth and remodeling.

Figure 5:
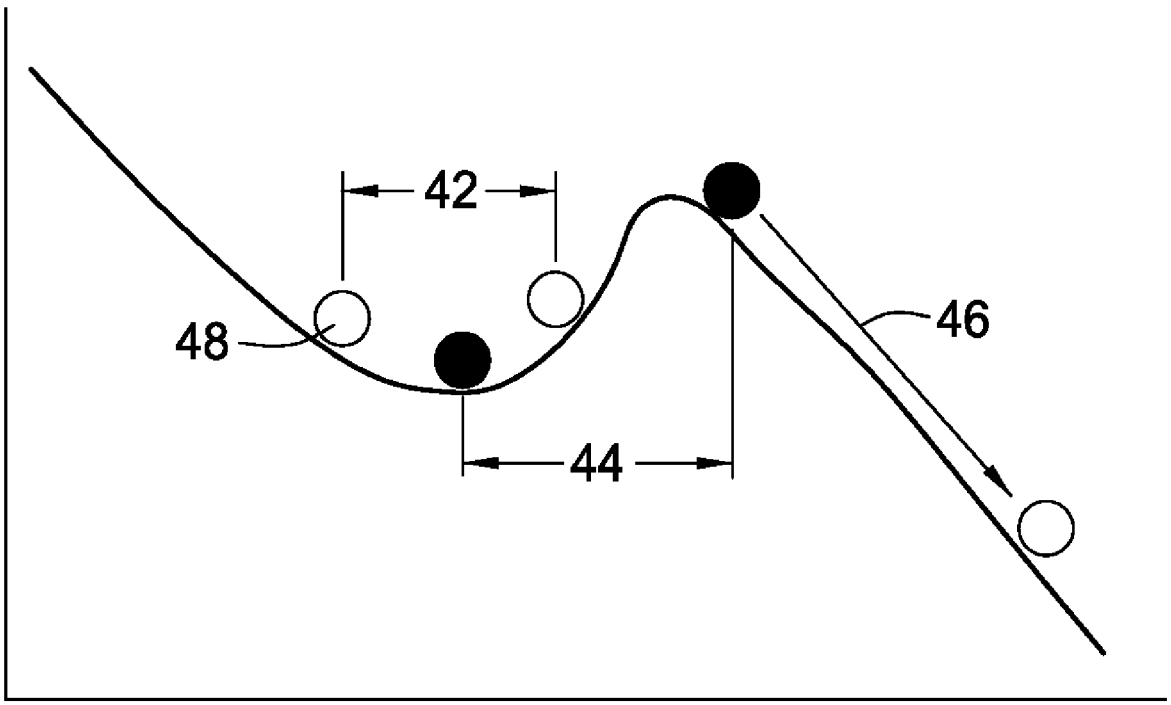
FIG. 5 is a graph that illustrates the growth stages in CHF.

FIG. 5 illustrates the "ball in a well" analogy for stability, instability and destabilizing events. The graph illustrates 3 regions the stable perturbations state 42, the destabilizing event 44 and the unidirectional unchecked progression 46. The PDR is the part of the curve that forms a well or the stable perturbations state 42 (i.e., where perturbations are met with restoration processes that bring the ball or heart back to an equilibrium or stable state). However, if there is a destabilizing event 44 such as a severe coronary stenosis that brings the heart (i.e., ball 48) outside of the stable perturbations state 42 or PDR, then a unidirectional, unchecked progression 46 or instability will ensue. For example, 68% of congestive heart failure cases are initiated by coronary artery disease, Gheorghaid and Bonow, 1998. Other stimuli, such as infection, over-pacing or atrial ventricular ("AV") shunting may also act as destabilizing events 44. This simplistic model for heart failure is supported by the fact that all these inducers or destabilizing events cause similar growth and remodeling (i.e., they result in a large, thin heart). Common statements such as "the heart is overloaded" suggests that the current state is unphysiologic or outside the stable perturbations state 42 or PDR. Moreover, treatments that "off-load the heart" are perhaps bringing the heart back into its PDR or stable perturbations state 42.

Although simplistic, such an instability paradigm is a model for heart failure. This model suggests that heart failure can be cured (via ventricular recovery) or prevented if the heart is off-loaded or returned to its PDR. Recent evidence supports such a mechanism for ventricular recovery. A recent modeling study (Guccione et al., 2001) suggests that wall stress is not an important inducer of the mechanical dysfunction in the borderzone of infarcts, thus it appears that strain or motion is the primary determinant. Hypokinetic or dyskinetic myocardium has aberrant motion despite possibly having a normal wall stress. The focus of preferred embodiments of the present invention is to push uniformly on the epicardial boundary during systole to restore the motion of the heart and eliminate hypokinesis and dyskinesis.

To model the treatment paradigm for embodiments of the present invention and grossly estimate what driving pressures are needed, one may use Laplace's law for a spherical vessel which gives an average wall stress ("σ") based on average radius ("R"), thickness ("H") and transmural pressure difference ($P_{in}-P_{out}$) where $P_{in}$ is the pressure in the ventricle and $P_{out}$ is the pressure outside the ventricle. In particular, $$\sigma=(P_{in}-P_{out})H/2R$$

Because blood is nearly incompressible, flow is dominated by pressure gradients (or less accurately by pressure differences). Without loss in generality, one may define blood pressure as its difference from atmospheric pressure. Because of rarification and densification, flows in compressible fluids are mediated by both pressure gradients and absolute pressure. Often $P_{out}$ is judiciously chosen as zero, yet for the present calculations, it is an important parameter because selected devices of the present invention are modulating $P_{out}$ by applying pressure to the epicardial surface of the heart.

The focus of some embodiments of the invention thus is to increase $P_{out}$ to obtain a lower σ and thus greater motion or ejection. For a large, thin, and hypokinetic heart, one may need to make σ at least as low as a normal heart.

Let $P_{in}$ be a typical mean systolic pressure (e.g., 7.5 kPa or approximately 100 mmHg). A typical thickness-to-radius ratio at end-diastole for a normal adult sheep is 1 to 2.5; whereas for overloaded, remodeled myocardium (as in the apical aneurysm model of Guccione et al., 2001) the thickness-to-radius ratio is about 1 to 4.

Using the equation above, to normalize σ with the same $P_{in}$, we would need a $P_{out}$ of 2.8 kPa. This is similar to the maximum driving pressure (approximately 3 kPa) used in in vitro tests described further in Example 2. For ventricular recovery, one will likely need external pressures that are about the same order as or slightly higher than pulmonary artery pressure. Hence, right ventricle ("RV") ejection fraction is expected to be nearly 100%. External pressure will be transferred through the incompressible RV myocardium and incompressible blood in the RV chamber, while RV outflow is accelerated. Kawaguchi et al. (1992) has demonstrated that uniform pressure applied to the entire epicardial surface will assist the heart at all levels of contractility.

Certain devices of the present invention can decrease RV input to compensate for the expected increase in RV output. Absent this capability it is likely that the RV and healthy regions of the LV would atrophy due to excessive off-loading. However, some devices of the present invention are ideal for weaning or gradually decreasing $P_{out}$, and the use of clenbuterol (Hons and Yacoub, 2003) has been shown to be useful in achieving ventricular recovery by preventing atrophy.

Devices and Implantation. To achieve a minimally invasive device of the class of the '619 application devices, a soft-shelled DCCD has been constructed according to certain embodiments of the present invention. The device has inflatable, longitudinally oriented chambers that when deflated are collapsible. In addition, the deflated chambers are shaped and adjoined to form a structure that allows typical diastolic configurations. When pressurized the chambers push on the exterior of the heart in such a way as to induce a systolic configuration with normal curvatures.

Figure 6B:
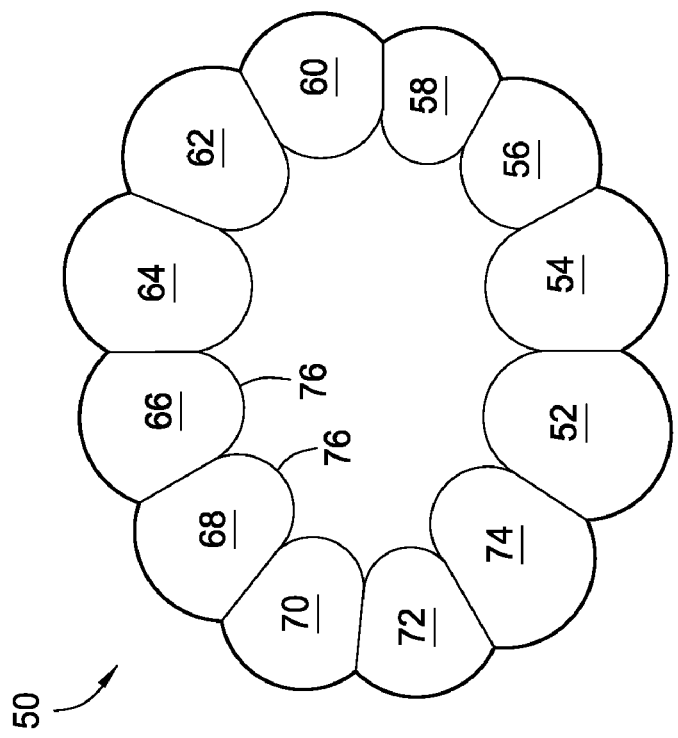
FIG. 6A is in the deflated state and FIG. 6B is in the pressurized state.
Figure 6A:
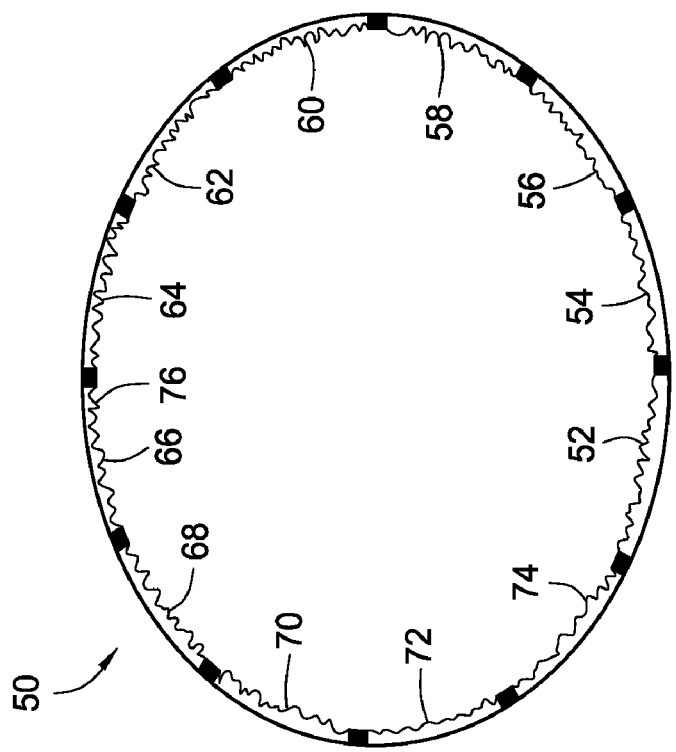

FIGS. 6A and 6B illustrate a horizontal cross section of one embodiment of the device 50 of the present invention in the deflated state FIG. 6A and the inflated state FIG. 6B. The device 50 includes 12 chambers 52-74 arranged with 4 chambers on the RV side and 8 chambers that are mostly on the LV but also overlapping the interventricular sulci. The chambers 52-74 are constructed from polyethylene film in one embodiment; however, other materials may be used. The side of the chambers 52-74 that are on the outer boundary form a shape that is similar to the end diastolic shape of the heart. The interior surface 76 has folds and crenulations such that when inflated the chambers 52-74 mostly expand inward.

FIGS. 7A and 7B illustrate a vertical cross section of one embodiment of the device 50 of the present invention in the deflated state FIG. 7A and the inflated state FIG. 7B. Device 50 includes chambers 52 and 64 in the inflated and deflated states. The interior surface 76 of the chambers 52-74 that are on the outer boundary form a shape that is similar to the end diastolic shape of the heart. The interior surface 76 has folds and crenulations such that when inflated the chambers 52-74 mostly expand inward to contact the epicardium 32 of the heart 30.

FIGS. 8A and 8B illustrate a horizontal cross section of one embodiment of the device 50 of the present invention fitted to the heart 30. FIG. 8A is in the deflated state and FIG. 8B is in the inflated state. The device 50 includes 12 chambers 52-74 arranged with 4 chambers on the RV side and 8 chambers that are mostly on the LV but also overlapping the interventricular sulci. The chambers 52-74 include interior surface 76 that contacts the epicardium 32 of the heart 30. The side of the chambers 52-74 that are on the outer boundary form a shape that is similar to the end diastolic shape of the heart. The interior surface 76 has folds and crenulations such that when inflated the chambers 52-74 mostly expand inward. The shape of the interior regions 34 and 36 can be compared in the inflated state FIG. 8B and the deflated state FIG. 8A.

FIGS. 9A and 9B illustrate a vertical cross section of one embodiment of the device 50 fitted to the heart 30 in the deflated state FIG. 9A and the inflated state FIG. 9B. Device 50 includes chambers 52 and 64 in the inflated and deflated states. The interior surface 76 of the chambers 52-74 that are on the outer boundary form a shape that is similar to the end diastolic shape of the heart. The interior surface 76 has folds and crenulations such that when inflated the chambers 52-74 mostly expand inward to contact the epicardium 32 of the heart 30. The shape of the interior regions 34 and 36 can be compared in the inflated state FIG. 9B and the deflated state FIG. 9A.

Figure 8:
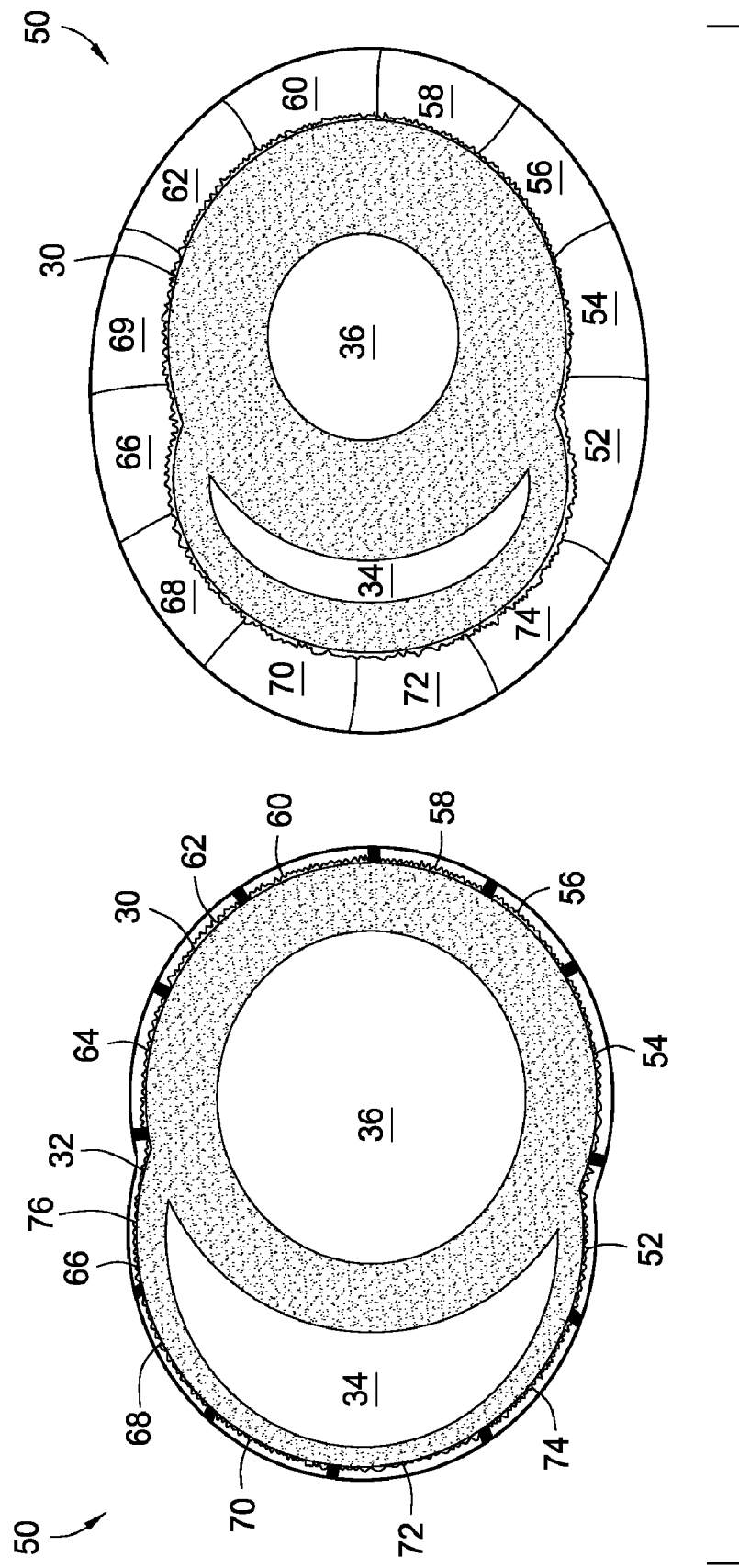

The fully pressurized shape without the heart inside is helpful for illustrating one device of the present invention, yet the shape will be significantly different when the device surrounds a heart which contains blood under pressure (see FIGS. 8 and 9). With a heart inside the pressure in the lumen of the device is higher than the pressure in the inflatable chambers. Because the chambers cannot fully expand, the inner film of the chambers is not taut. Rather than being supported by tension in the film (e.g., the right side of FIG. 6), pressure on the lumen side of the longitudinal chambers is supported by contact forces on the epicardial surface, e.g., the right side of FIG. 8. Without tension on the inner film, the attachment points are not drawn inward, e.g., the right side of FIG. 6. Instead, the shape of the outer sides of the chambers becomes circular to support the pressure within the chambers, e.g., the right side of FIG. 8. Note how the inner membrane is crenulated and thus not under tension. Consequently, the pressure in the device chambers applies direct pressure to the heart surface. In a similar manner, a blood pressure cuff applies direct pressure to the surface of a patient's arm.

Because the inflatable chambers taper (as they go from base to apex) in a manner that resembles natural cardiac curvature (see FIG. 7, right panel) the apex of the heart will have a physiological curvature. Moreover, because the device is rigid when pressurized, the curved shape of the apical end will act to prevent the heart from being expelled from the device. Basically, for the heart to leave the device the apical shape would have to pucker or a vacuum would need to form in the apical end of the device, both of which are unlikely.

Figure 10:
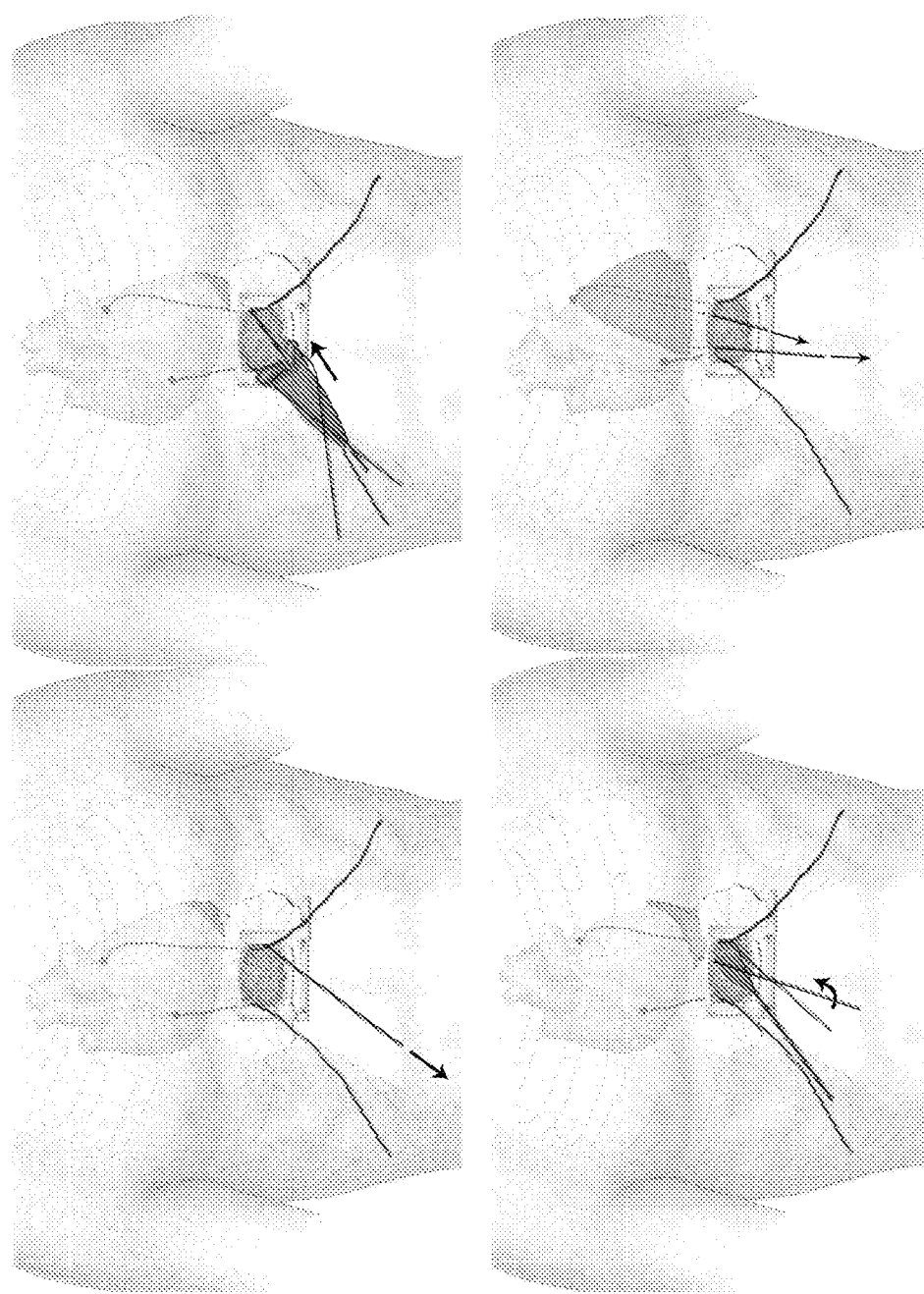
FIGS. 10A to 10D show a time series of the implantation method according to one embodiment of the present invention.

FIG. 10 diagrams one implantation method. Consequently, the device may be implanted with minimal attachment or sewing to the heart. Clamps on the atrial appendages are sufficient and useful for sensing the ECG or for pacing the heart. The access port on the apex (i.e., the hole in the bottom of the device) is useful for implantation and for removing fluid that could accumulate between the heart and device. Additionally, a biocompatible lubricant, anti-clotting, anti-fibrosis, or antibiotic agent may be injected into the space between the heart and device. So that the device may be removed easily after weaning, the device may be covered with a film that retards fibrous adhesions, e.g., SURGI-WRAP®.

As noted above, because the RV operates at a lower pressure and has a thin wall, certain DCCDs of the present invention will enhance RV ejection more than LV ejection. As observed in the implantation of a prototype, driving pressures that are equal to or greater than pulmonary artery pressure may occur, resulting in a 100% RV ejection fraction is expected. Pulmonary congestion may result if RV output is continuously increased relative to LV output. Autoregulatory mechanisms may mitigate this enhancement of RV ejection over LV ejection. If not, separation of RV and LV chambers in the DCCD may be useful. In particular, it may be possible to impede RV filling with residual pressurization of the 4 RV chambers during diastole. By controlling input to the RV we may modulate the ratio of RV output to LV output. Pulmonary congestion was not seen in the implantation of at least one prototype of a hard shelled device, but this may have been due to tricuspid regurgitation rather than to autoregulatory mechanisms adjusting to the increase in RV ejection fraction. Because of the regurgitation, forward flow was not enhanced.

Figure 11:
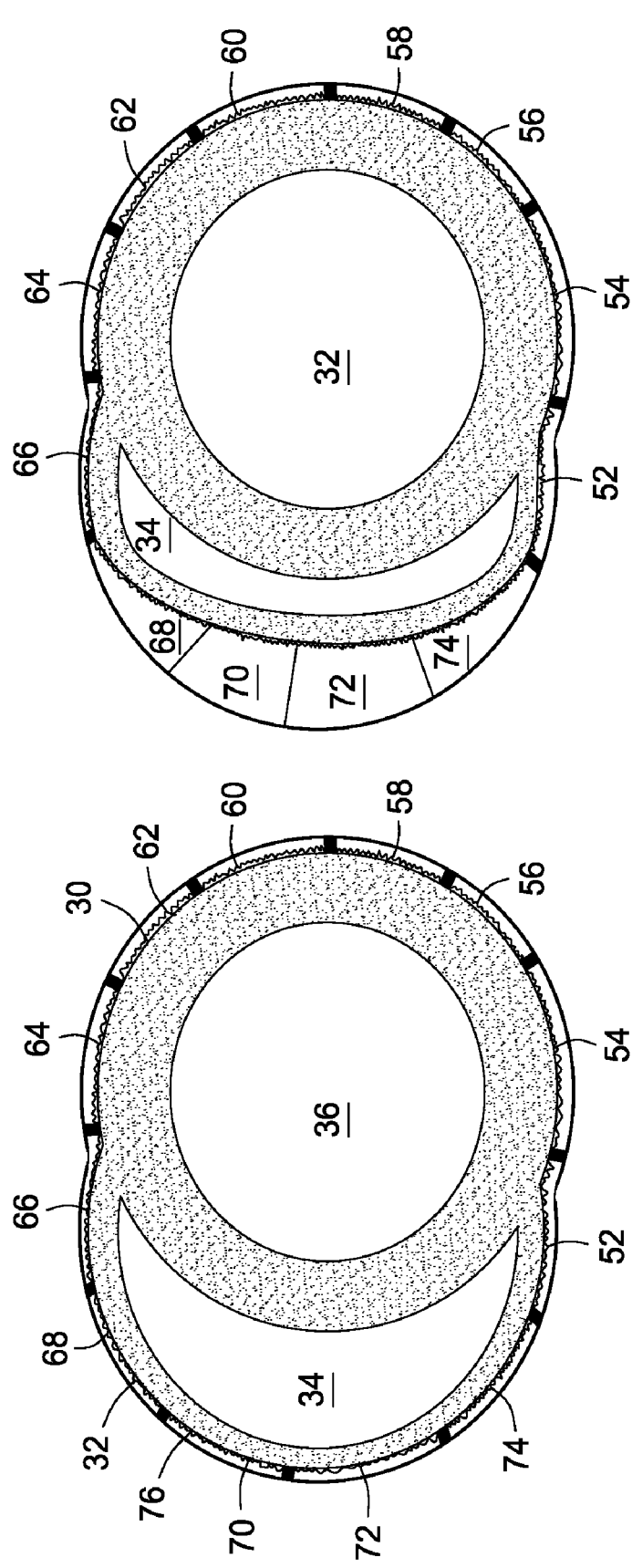
FIG. 11 is a schematic diagram of one embodiment of the present invention configured to reduce right ventricle input by reducing right ventricle filling.

FIG. 11 illustrates how RV input (i.e., filling) can be modulated by the application of residual RV epicardial pressure (RRVEP). During diastole the myocardium is relaxed and the heart shape is easy to perturb. This is particularly true of the RV freewall because it is very thin. Hence, residual gas in the four chambers abutting the RV freewall will likely prevent the RV from filling while leaving the LV unperturbed. It is, in essence, easier to differentially modulate filling than to modulate ejection.

FIGS. 11A and 11B illustrate a horizontal cross section of one embodiment of the device 50 of the present invention fitted to the heart 30. FIG. 11A is in the deflated state and FIG. 11B is in the inflated state. The device 50 includes 12 chambers 52-74 arranged with 4 chambers on the RV side and 8 chambers that are mostly on the LV but also overlapping the interventricular sulci. The chambers 52-74 include interior surface 76 that contacts the epicardium 32 of the heart 30. The side of the chambers 52-74 that are on the outer boundary form a shape that is similar to the end diastolic shape of the heart. The interior surface 76 has folds and crenulations such that when inflated the chambers 52-74 mostly expand inward. The shape of the interior regions 34 and 36 can be compared in the inflated state FIG. 11B and the deflated state FIG. 11A.

A potential drawback is that the RV freewall may atrophy because RV volume will be chronically decreased and native RV stroke work will be decreased. Fortunately, a device that proactively modulates the strain pattern is ideal for weaning the heart from a device because assist can be graded. Most previous DCCDs only assist when the heart is weak enough to be grossly deformed.

The following examples are provided to further explain specific examples of the invention. They are not intended to represent all aspect of the invention in its entirety. Variations will be apparent to one skilled in the art.

Example 1

Figure 12:
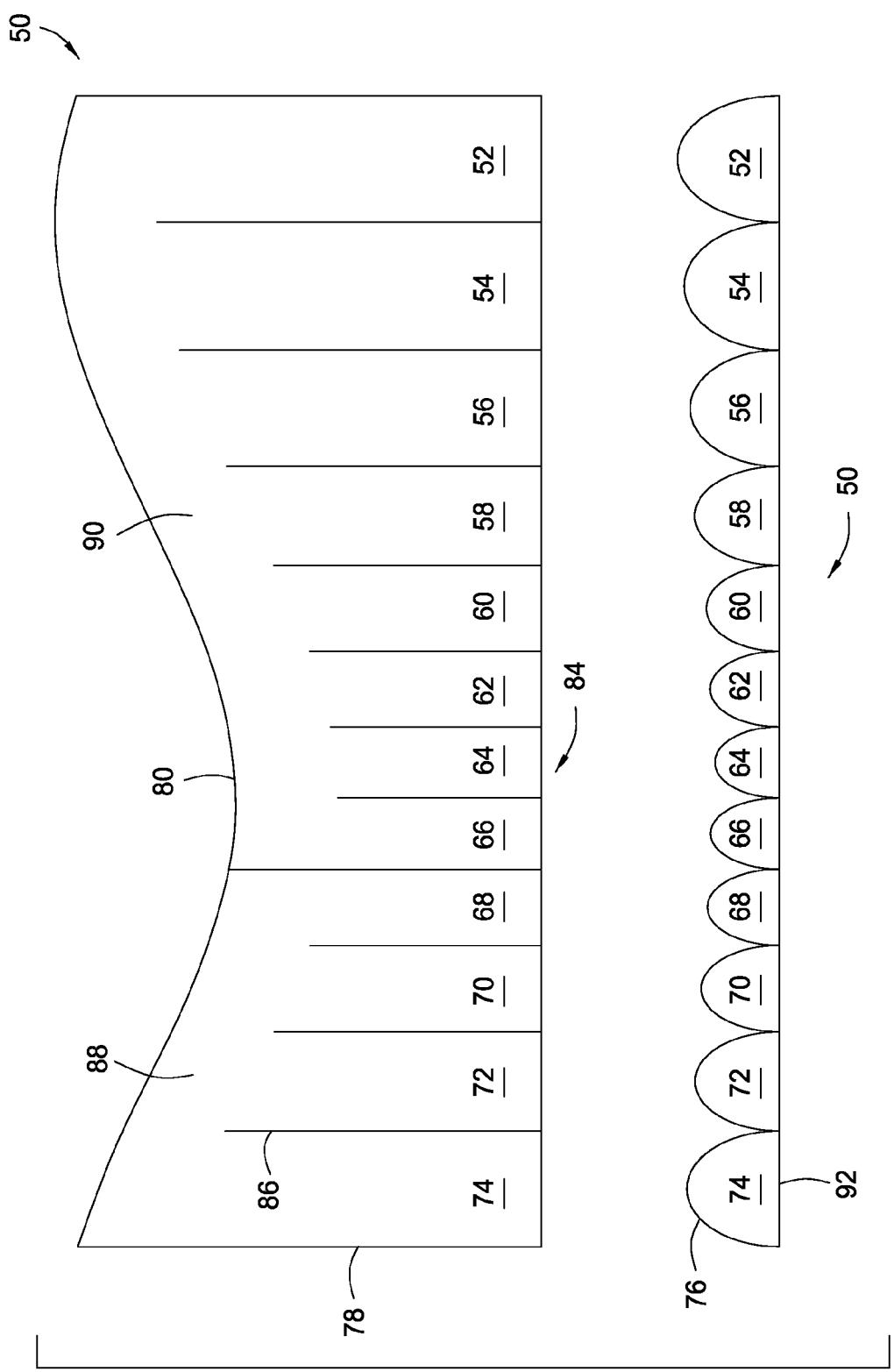
FIG. 12 is a schematic diagram illustrating the layout of a first series of heat welds between two polyethylene sheets.

Direct Cardiac Compression Device. FIGS. 12A and 12B are front view and horizontal cross sectional view of the present invention respectively. FIG. 12A illustrates the device 50 having a surface 78 having a basal edge 80 and an apical edge 84. The surface 78 includes welds 86 to form the chambers 52-74 and include the 4 right ventricle chambers 88 and the 8 left ventricle chambers 90. FIG. 12B illustrates the device 50 having an interior surface 76 on the endocardial side and an exterior surface 92 on the pericardial side. Welds 86 are used to form the chambers 52-74. In some embodiments, the interior surface 76 is made of two mils thick polyethylene and the exterior surface 92 is made of 6 mils thick polyethylene; however the skilled artisan will recognize other thickness (e.g., 0.1 to 12 mils) and other materials may be used.

Figure 13:
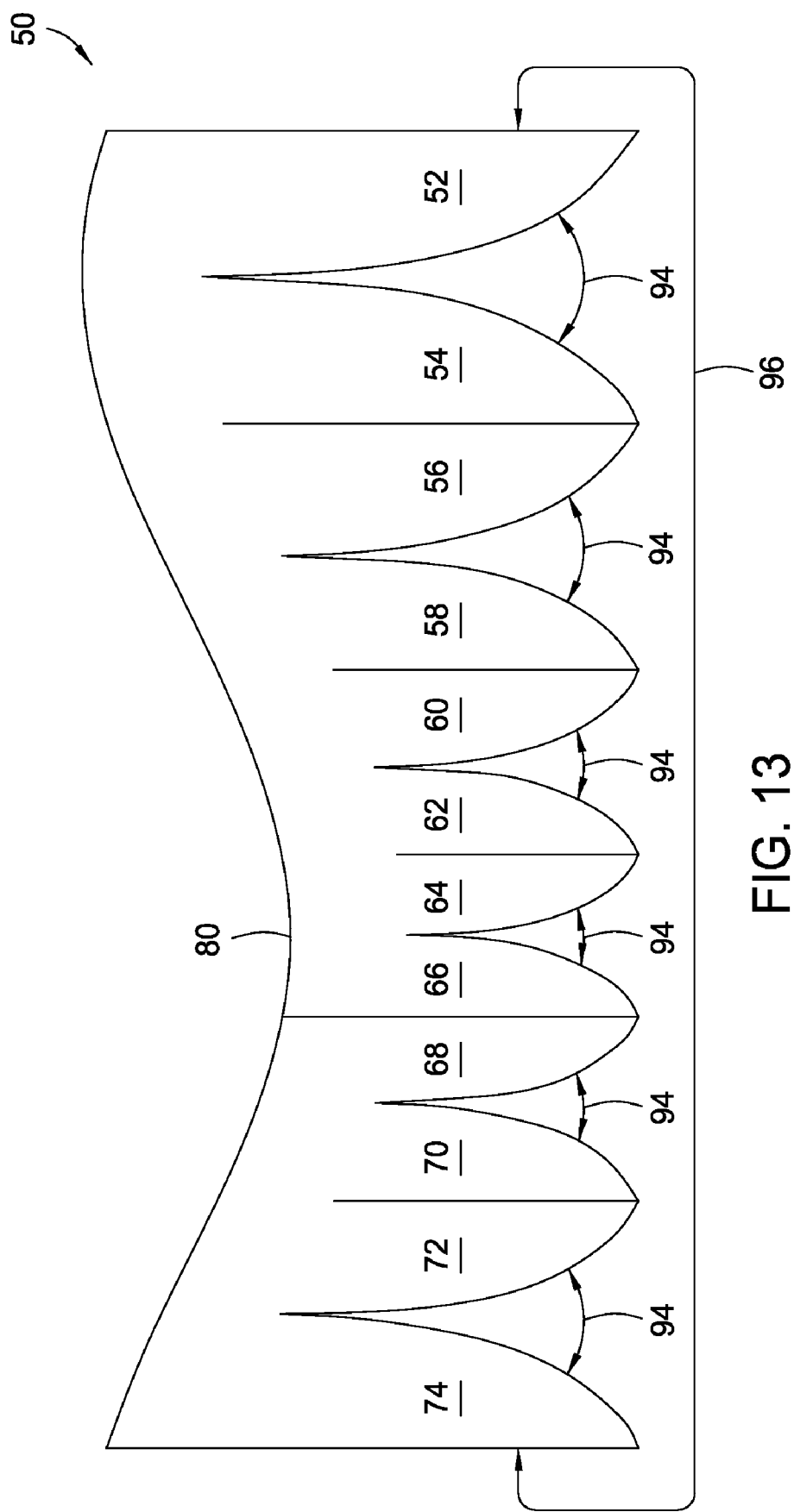
FIG. 13 is a schematic diagram illustrating the layout of the second and third series of heat welds to produce a device according to an embodiment of the present invention.

By heat welding two polyethylene sheets together along particular folds (as see in FIGS. 12 and 13), a prototype DCCD according to an embodiment of the invention was constructed (see FIG. 14). FIG. 13 illustrates the device 50 having a surface 78 having a basal edge 80 at the basal end of posterior interventricular sulcus. A second weld 94 is used to secure the chambers 52-74 and the device 50 is completed by a third weld 96 to the device in FIG. 14.

Except for the crenulations, the first two series of welds were done with the sheets lying flat. Upon completing the third series of welds, the device took on its 3D final shape. To make the heat welds, brass rods (for the straight welds) and bent copper plates (for the curved welds) were heated in an oven at about 180° C. for about 1 hour and then held against the sheets at the proper position for about 40 seconds. A non-stick polymer (e.g., Hama Inc) was placed between the bars and the polyethylene sheets. The polymer was designed for household crafts, which involve melting plastics with a clothes iron. The pneumatic drive lines (see FIG. 14, but not shown in FIGS. 12 and 13) were inserted through grommets fastened to the device with gaskets to seal the attachment and avoid stress risers. Additionally, there is an apical hole in the device, which was made by blunting the apical tips of the 12 chambers. To be more specific, the hole is not in the chambers, but the chambers do not come together at the apical end, thus leaving a hole. Through this hole one may remove fluid or air that accumulates between the device and the heart.

A custom MATLAB® program was written to calculate the weld layouts from the following three cardiac measurements that could be obtained from a cardiac ultrasound (at end-diastole): 1) distance from apex to base along the posterior epicardial boundary, 2) distance from apex to base along the anterior epicardial boundary, and 3) perimeter of the epicardial boundary from a short axis slice parallel to the valve plane at the level of the papillary tips. The output for an adult ovine heart obtained from the slaughterhouse was calculated. From the output the weld lines were transferred to the outer (uncrenulated) sheet. FIG. 14 shows the completed device with the ovine heart inside it and layout markings on the outer sheet.

In addition, the device of the present invention may contain multiple chambers each independently controllable to allow customizing of the device for a particular condition. For example, one embodiment includes 12 chambers with 2 chambers that allow the pressure of the chambers to be regulated independently.

Example 2

In Vitro Testing. The device of Example 1 was tested on the benchtop and loaded with about 9 kPa of pressure. Based on previous experiments with an earlier device, it was expected to use driving pressures below 5 kPa. An important finding from this benchtop test was that the heart was not ejected from the device when the device was pressurized. This is an important design feature because sewing to the heart will not be needed and interference with the heart valves will be minimal. There were small leaks in the device, but leak proof devices are not required for most uses. Instead, one may place drains to vacuum on the apical end: one in the apical hole to remove air and fluid between the device and heart, and one to remove air and fluid between the device and mediastinum. Lost pneumatic driving fluid may be replaced as necessary.

This embodiment has also been tested in a live sheep, as expected from the benchtop trials, the device could be easily slipped over the heart utilizing a sub-xiphoid incision. Moreover, without any attachments (i.e., sewing, clamping, or the like) the heart remained within the device (i.e., it was not ejected) during pressurization of the device.

The present invention provides a direct cardiac compression device (DCCD) that applies forces to the exterior, epicardial boundary of the heart. The device of the present invention has a shape with curvatures that are similar to the end-diastolic shape of the heart at the end-diastole of the cardiac cycle. In addition, it may be enabled to purposely restrict inflow to the right side of the heart, e.g., right-sided inflow restriction ("RSIR"). When it is enabled for RSIR, the device protrudes inward towards the right ventricle during diastole to decrease the end-diastolic volume of the right ventricle. Regardless, the present invention enables (or induces) the left ventricle to assume a shape with curvatures that are similar to the proper end-diastolic shape of the heart.

At end-systole of the cardiac cycle, the present invention has a shape with curvatures that are similar to the proper end-systolic shape of the heart. The present invention is active in the sense that energy is consumed to accomplish the shape change during systole and energy is liberated to accomplish the shape change during diastole. The energy source is from a pneumatic pressure source. During systole (i.e., shape change from end-diastole to end-systole) the device is inflated with a positive pressure. During diastole (i.e., shape change from end-systole to end-diastole) the device is deflated via suction. If enabled for RSIR, the device is not fully deflated during diastole because some residual pressure is applied to chambers that abut the right ventricle.

The present invention is soft or collapsible when deflated. In addition, the present invention minimizes the risks of thrombosis and infection as there is no contact with the blood. Many of the devices in the art when pressurized are grossly abnormally shaped, evidenced by the various schemes used to attach the DCCD to the heart (e.g., sewing to ventricle, basal drawstring, apical suction cup, etc).

There is no need to attach the present invention to the heart because the heart is naturally drawn into the pressurized or activated device. Specifically, for the heart to leave the device (i.e., be extruded from the DCCD), the device curvature would need to invert, yet the device rigidity (when pressurized) resists curvature inversion. This is very useful because implantation time and complications due to attachment are minimized, i.e., when the activated shape of the device cavity (i.e., the inner wall of the DCCD which touches the epicardial or outer boundary of the heart) is nearly end-systolic shape. It can eliminate dyskinesis (defined as abnormal cardiac motions). Current evidence indicates that growth and remodeling in the heart are guided by mechanical stimuli such as the motion during cardiac contraction whereby the elimination of dyskinesis is of paramount importance. The device provides some of the pumping power demanded of the heart to energize or pressurize the circulatory system. Abnormal hearts often need to be "off-loaded" or be assisted with satisfying the circulatory demands of the body. In contrast, passive devices like Corcap or the Myosplint cannot provide power for pumping blood.

The device can be implanted in a minimally invasive manner through, for example, a small sub-xiphoid incision. Also, it enables a failsafe mechanism. In particular, the device does not hinder cardiac performance when the device is deflated or deactivated. In the embodiments herein, we completely deflate the device (default to vacuum) to make it soft and collapsible.

FIGS. 15A-15D are images that illustrate another embodiment of the present invention that includes one pressure chamber with eight interior supports in a fan-like arrangement. FIGS. 15A and 15B are images of the device without the outer covering attached, while FIGS. 15C and 15D are images of the device with the outer covering attached.

The purpose of the interior (inside the chamber as opposed to inside the cavity formed by the inner boundary of the DCCD) supports is to make the pressurized shape like the end-systolic shape of the heart. In similar fashion, the interior supports of an air mattress make the pressurized shape that of a mattress as opposed to that of spheroid. This prototype is made of latex, yet a device for implantation would be made of a flexible biocompatible polymer such as polyurethane. Being made of a highly flexible material, it is collapsible. The apical hole in the device is a useful feature that aids with implantation, e.g., by being able to draw the heart apex into the device via a suction cup threaded through the apical hole in the device. The apical hole is also useful for removing any fluid or air that leaks out of the device that would accumulate between the heart and device.

Figure 16:
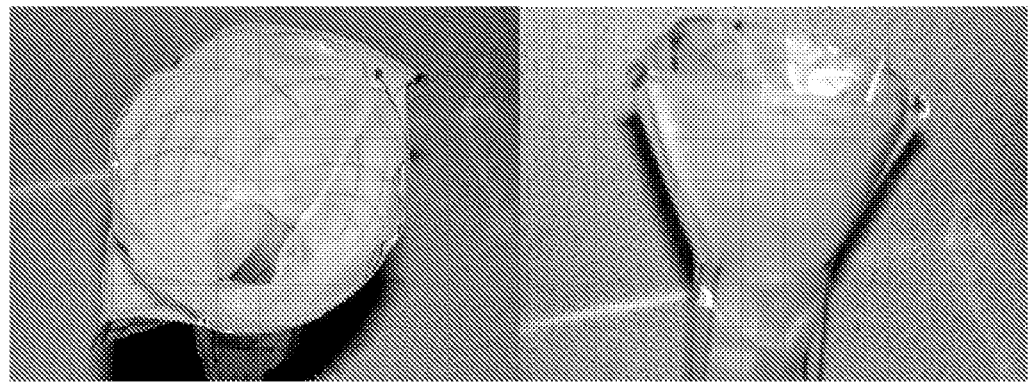
FIG. 16 is an image that illustrates a device according to another embodiment of the present invention.

FIGS. 16A-16B are images that illustrate yet another embodiment of the present invention that includes supports interior to the chamber, however, it has a support interior to the cavity. Similar to the embodiment depicted in FIG. 15, this embodiment is a one chamber device; however rather than have supports interior to the chamber there are supports interior to the cavity. In particular, there are wires weaved to form a shape appropriate for the heart. When pushed on by the expanding chamber during systolic pressurization the wire weave allows the cavity to shrink, yet they force the cavity to have a curvature that is normal for end-systole. Wires made of super elastic metals like Nitinol allow the device to be soft or compressible for insertion. Pictures of this embodiment are below. Other metals that may be used include shape-memory alloys like copper-zinc-aluminum, iron-manganese-silicon, gold-cadmium, copper-aluminum, copper-aluminum-nickel, and nickel-titanium.

Figure 17:
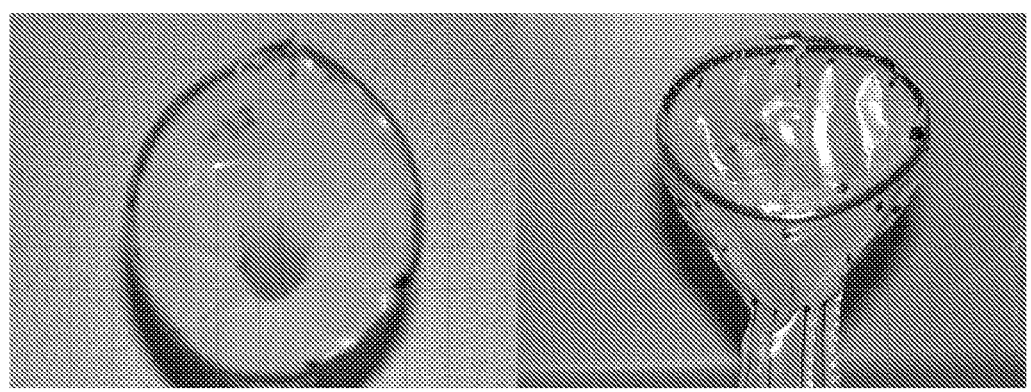
FIG. 17 is an image that illustrates a device according to yet another embodiment of the present invention.

FIGS. 17A-17B are images that illustrate still another embodiment of the present invention that includes supports interior to the chamber; however, it has a support interior to the cavity. Rather than wires made of super elastic metals that allow the device to be soft or compressible for insertion, this embodiment has six separate chambers, and the chamber dividers act as supports. When pushed on by the expanding chamber during systolic pressurization the cavity can shrink, yet they force the cavity to have a curvature that is normal for end-systole. This embodiment has been tested in 4 sheep and it was implantable in a minimally invasive fashion, failsafe, and able to eliminate dyskinesis caused by a myocardial infarction (heart attack). Also, by inflating the two chambers that abut the right ventricle, the central venous pressure was caused to rise by restricting the filling.

Figure 18:
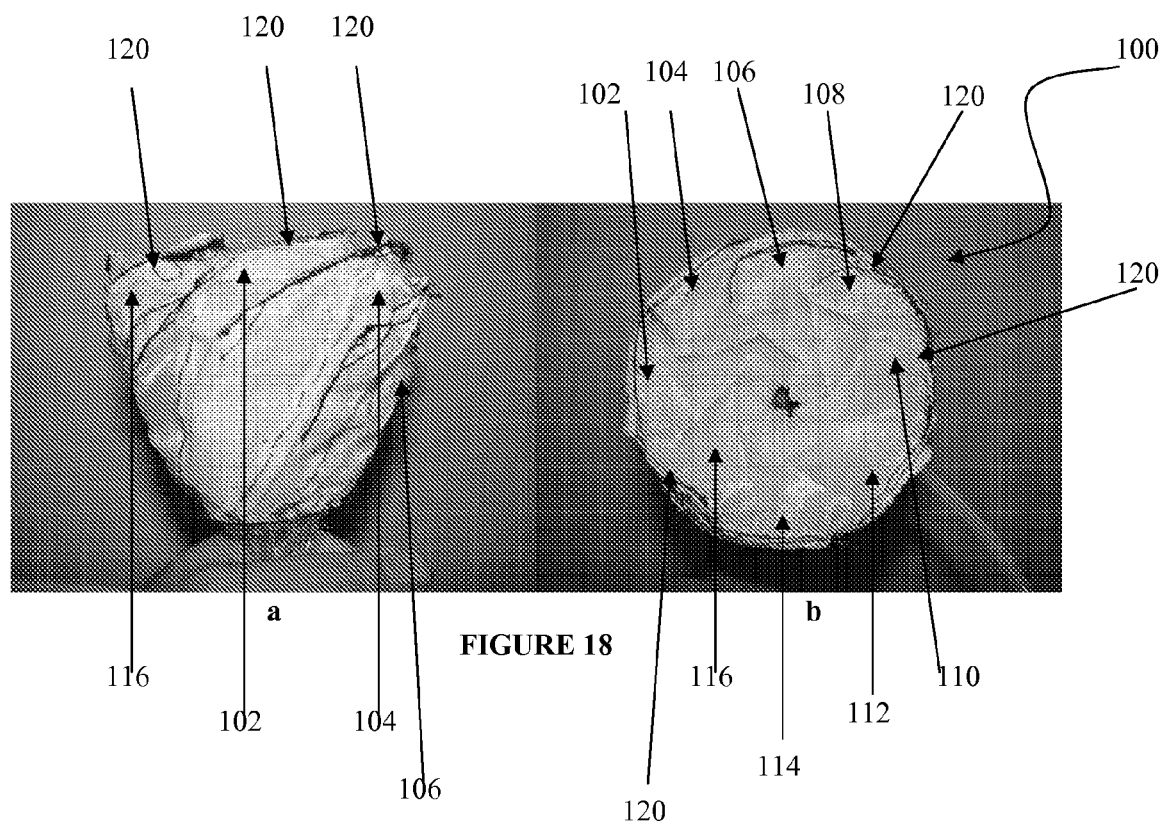
FIG. 18A is a side view and 18B is a top view of another embodiment of the present invention.

FIG. 18A is a side view and 18B is a top view of another embodiment of the present invention having a passive resilient inner panel. The device 100 includes 8 separate partially overlapped membranes 102-116 sewn together to form the cup shaped device. FIG. 18A illustrates overlapped membranes 102, 104 and 116 of device 100. The top view of FIG. 18B illustrates the overlapped membranes 102, 104, 106, 108, 110, 112, 114 and 116 in a partial overlapping arrangement. Each of the overlapped membranes 102-116 is like a petal with the outer edge of one overlapped membrane 102-116 attached of the adjacent overlapped membrane 102-116 and the at the inner edge of the overlapped membrane 102-116 free to move. Each of the overlapped membranes 102-116 consists of nylon cloth surrounding a bladder (not shown). The bladder (e.g., polyurethane bladders) (not shown) may be inserted into the apical end 118 of the overlapped membranes 102-116. A suture tie may used to secure the bladders (not shown) at the apical end 118 of the overlapped membranes 102-116. Encasing the bladder in a nylon shell of the device 100 permits each of the overlapped membranes 102-118 to be inflatable and sewn together and enhances durability. In addition, one or more resilient members 120 (e.g., memory metals like nickel-titanium alloy) are incorporated into each of the overlapped membranes 102-116. The materials may be connected by fusing, gluing, epoxing, sewing or other methods known to the skilled artisan. The overlapped membranes 102-116 form an interior surface has folds, overlaps and crenulations such that when inflated the overlapped membranes 102-116 mostly expand inward to contact the epicardium (not shown) of the heart (not shown).

Figure 19:
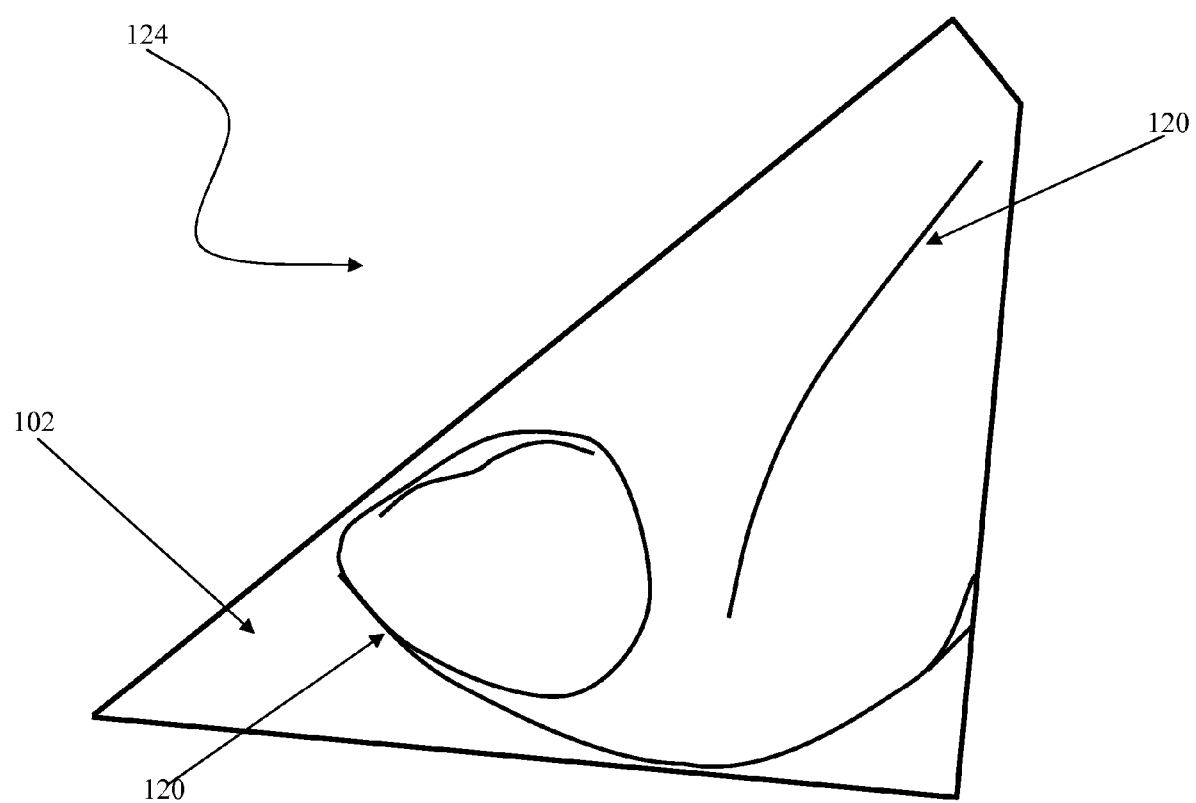
FIG. 19 is an image of the template used to construct the individual components of the present invention.

FIG. 19 is an image of the overlapped membrane template 124 used to construct the individual components of the present invention. The overlapped membrane template 124 shows where to attach each of the overlapped membranes 102-116 to the next overlapped membrane (not shown) to create one resilient inner panel (not shown). The resilient members 120 are affixed (e.g., sewn, glued, epoxied etc.) to the overlapped membranes 102-116, and once the overlapped membranes 102-116 were sewn together, the bladders (not shown) are inserted into the apical end (not shown) of the overlapped membranes 102-116.

Figure 20A:
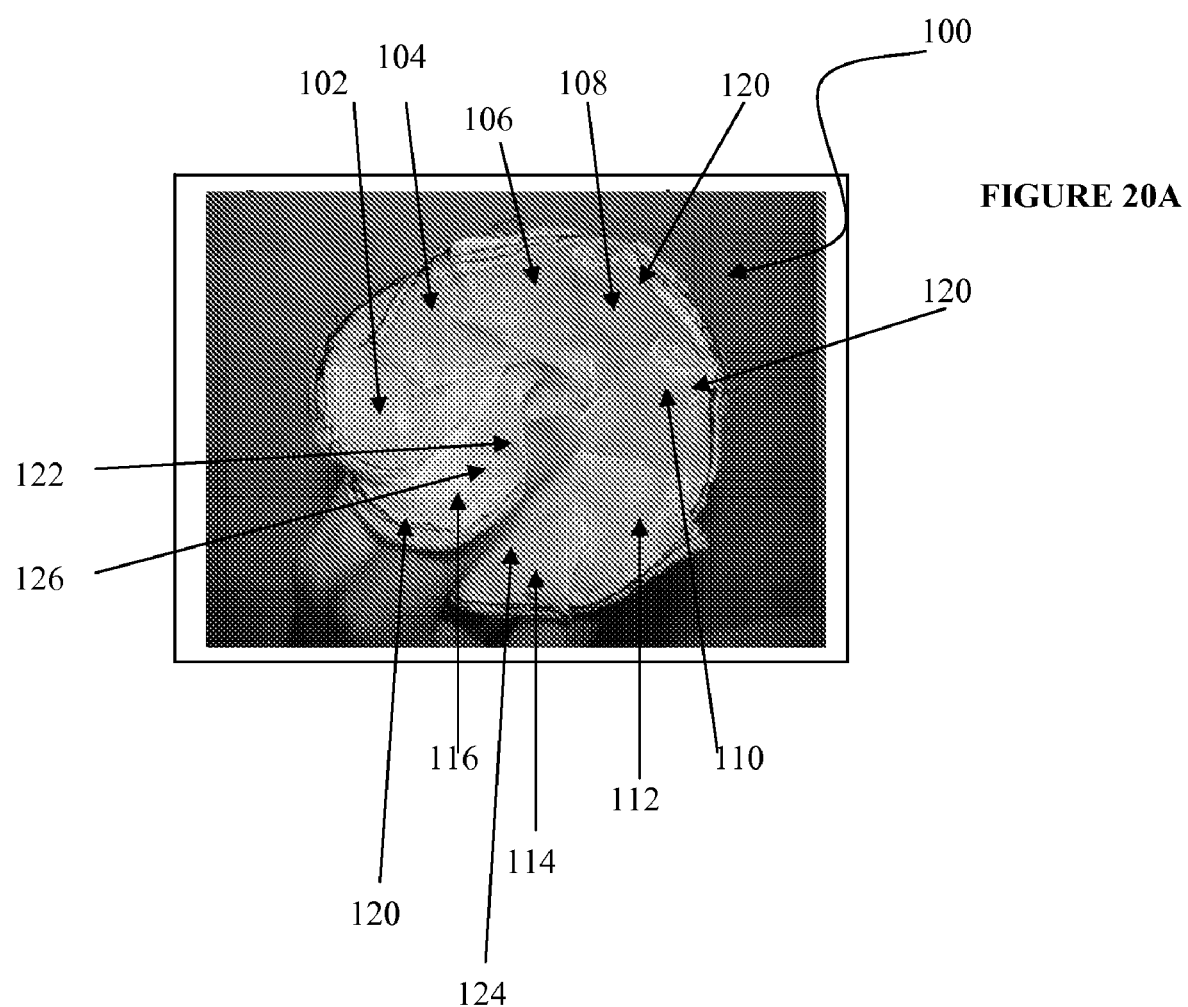
FIG. 20A is an image that illustrates the free, inner edge of a device according to another embodiment of the present invention
Figure 20B:
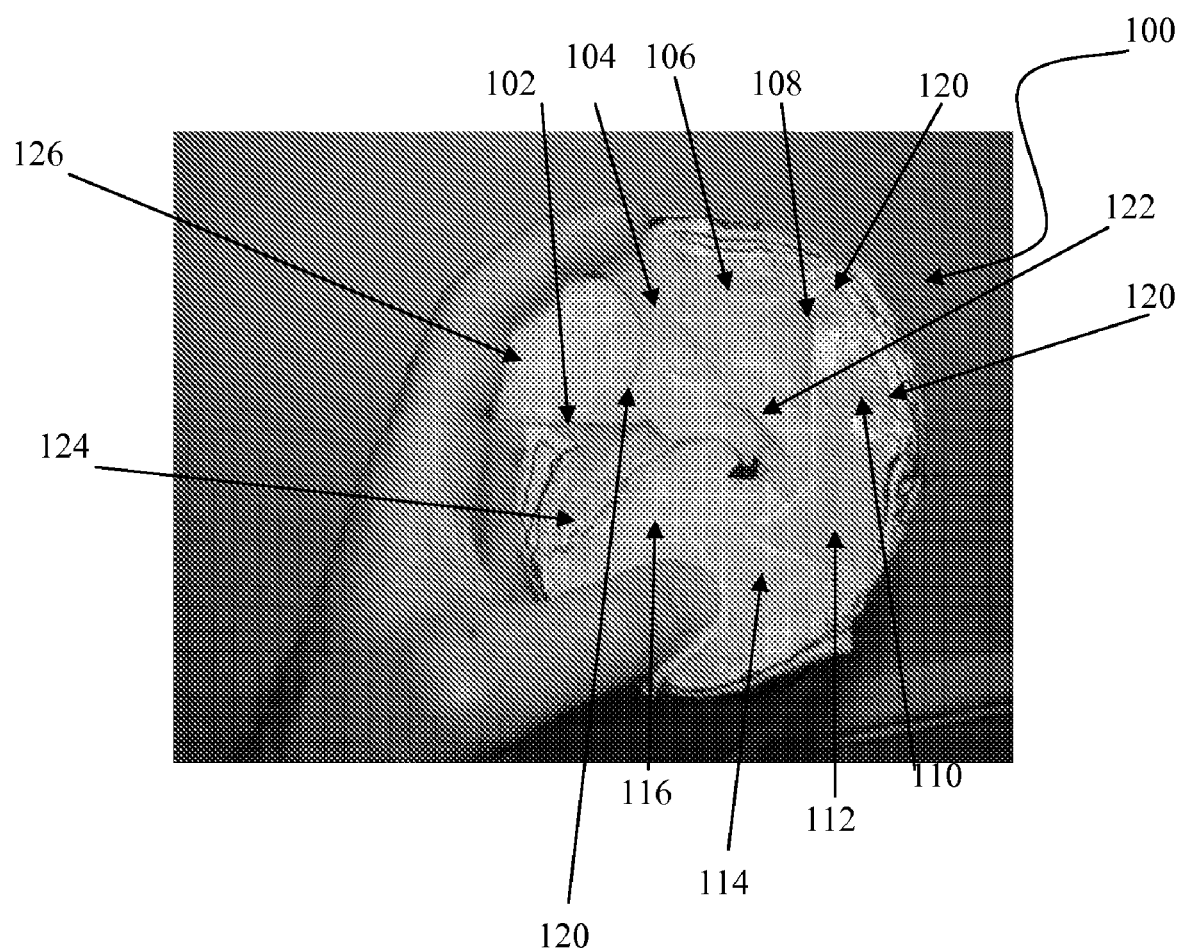
FIG. 20B is an image that illustrates the attached outer edge under the reflected up free edge.

FIGS. 20A and 20B are top views of another embodiment of the present invention that illustrates the free, inner edge of an overlapped membrane. The top view of FIGS. 20A and 20B illustrates the overlapped membranes 102, 104, 106, 108, 110, 112, 114 and 116 in a partial overlapping arrangement. Each of the overlapped membranes 102-116 include one or more resilient members 120 (e.g., memory metals like nickel-titanium alloy) incorporated into each of the overlapped membranes 102-116. FIG. 20A is an image that illustrates the free, inner edge 122 of the overlapped membrane 104 of the device 100. The top surface 124 of the overlapped membrane 104 is overlapped by the bottom surface (not shown) of the overlapped membrane 102. The bottom surface (not shown) of the overlapped membrane 104 overlaps the top surface (not shown) of overlapped membrane 106. The overlapping arrangement and the orientation of the attached outer edge and the free inner edge 122 is depicted in FIG. 20B. The overlapped membrane 102 and 104 are positioned to display the overlap of the top surface 124 of the overlapped membrane 104 and the bottom surface 126 of the overlapped membrane 102. The attachment of the overlapped membranes 102 to 104 create a free inner edge 122, that is relatively free to move inward to contact the epicardium (not shown) of the heart (not shown).

Figure 21A:
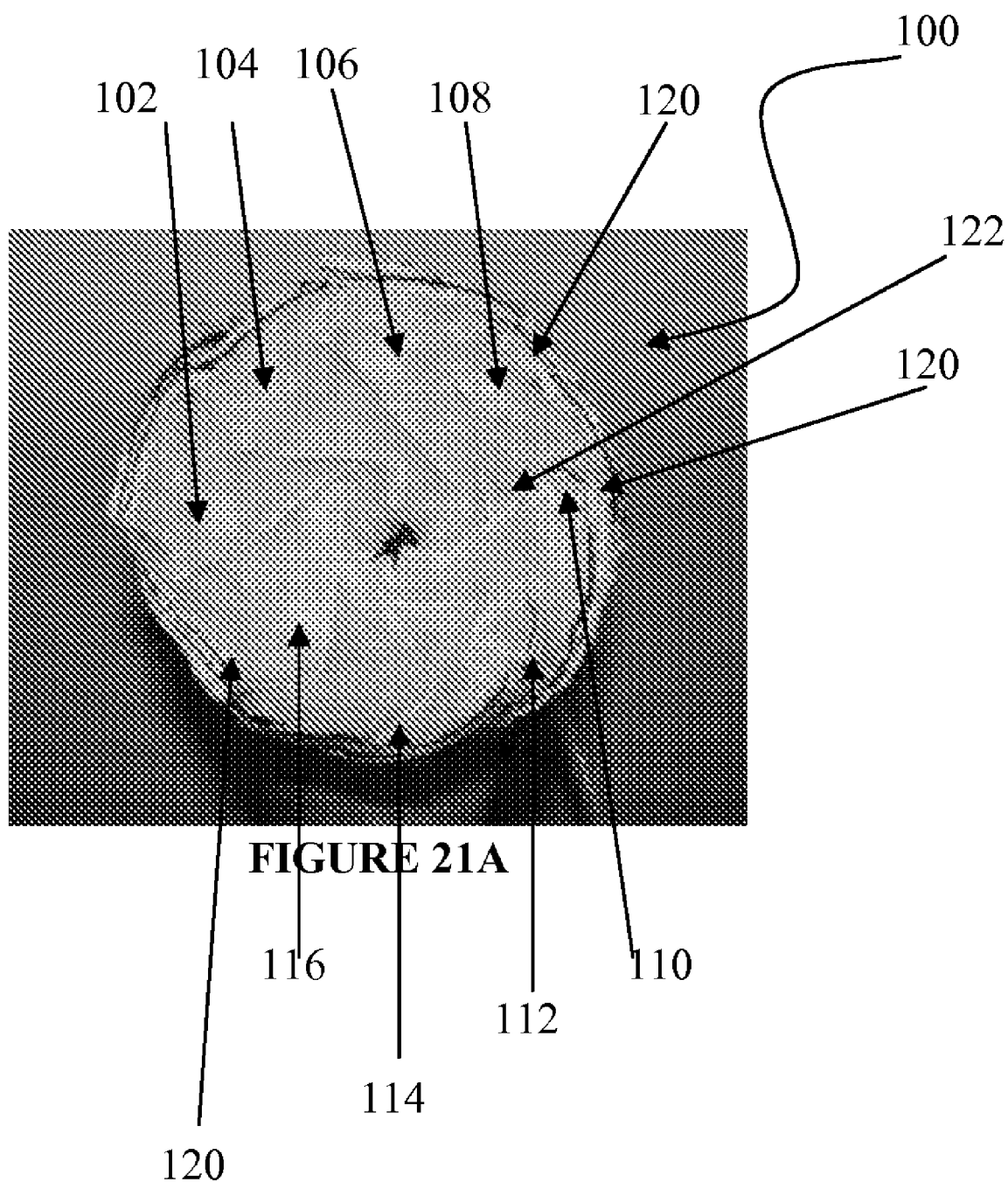
Figure 21B:
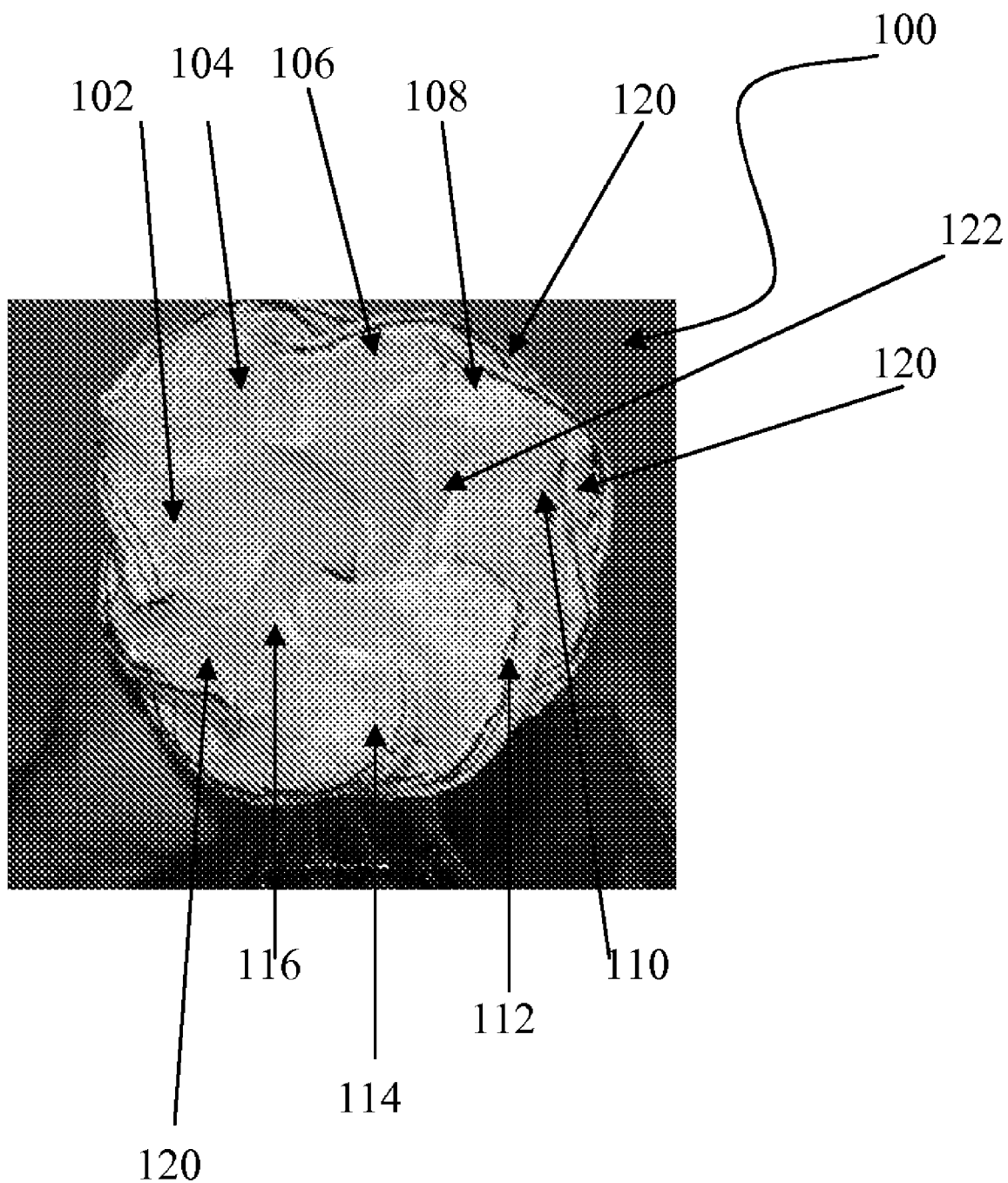
FIG. 21B is an image that illustrates a device having inflated bladders.

The top view of FIGS. 21A and 21B illustrates the overlapped membranes 102, 104, 106, 108, 110, 112, 114 and 116 in a partial overlapping arrangement. FIG. 21A is an image that illustrates a device having uninflated bladders, while FIG. 21B is an image that illustrates a device having inflated bladders. Each of the overlapped membranes 102-116 include one or more resilient members 120 (e.g., memory metals like nickel-titanium alloy) incorporated therein. The overlapping arrangement and the orientation of the attached outer edge and the free inner edge 122 create an epicardium chamber 130 with the apical aperture 128 remaining visible at the apical end 118. The bladders protrude inward, but do not obliterate the epicardium chamber 130. The inflation of the bladders result in the overlapped membranes 102-116 protrude inward, but the epicardium chamber 130 is not obliterated and the apical aperture 128 remaining visible at the apical end (not shown). By not obliterating the epicardium chamber 130, the heart is naturally or intrinsically contained in the device without suture or similar attachment to the heart.

Figure 22A:
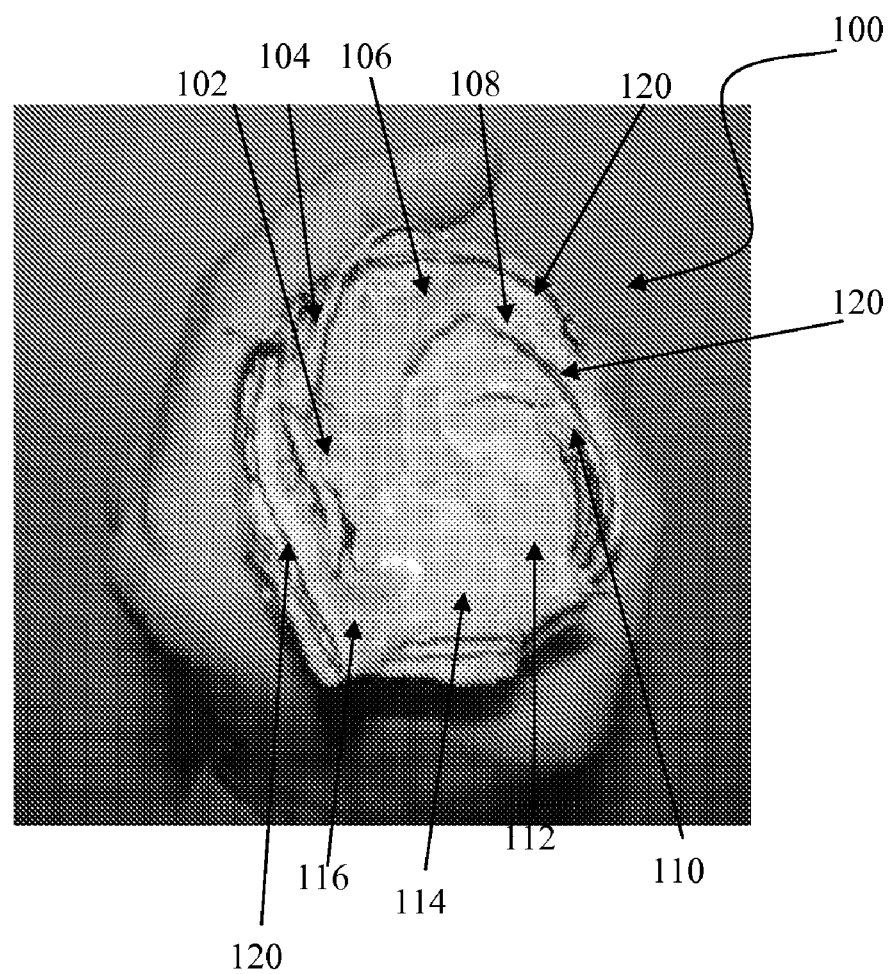
FIGS. 22A, 22B and 22C are images that illustrate a device according to one embodiment of the present invention expanding from collapsed configuration.
Figure 22B:
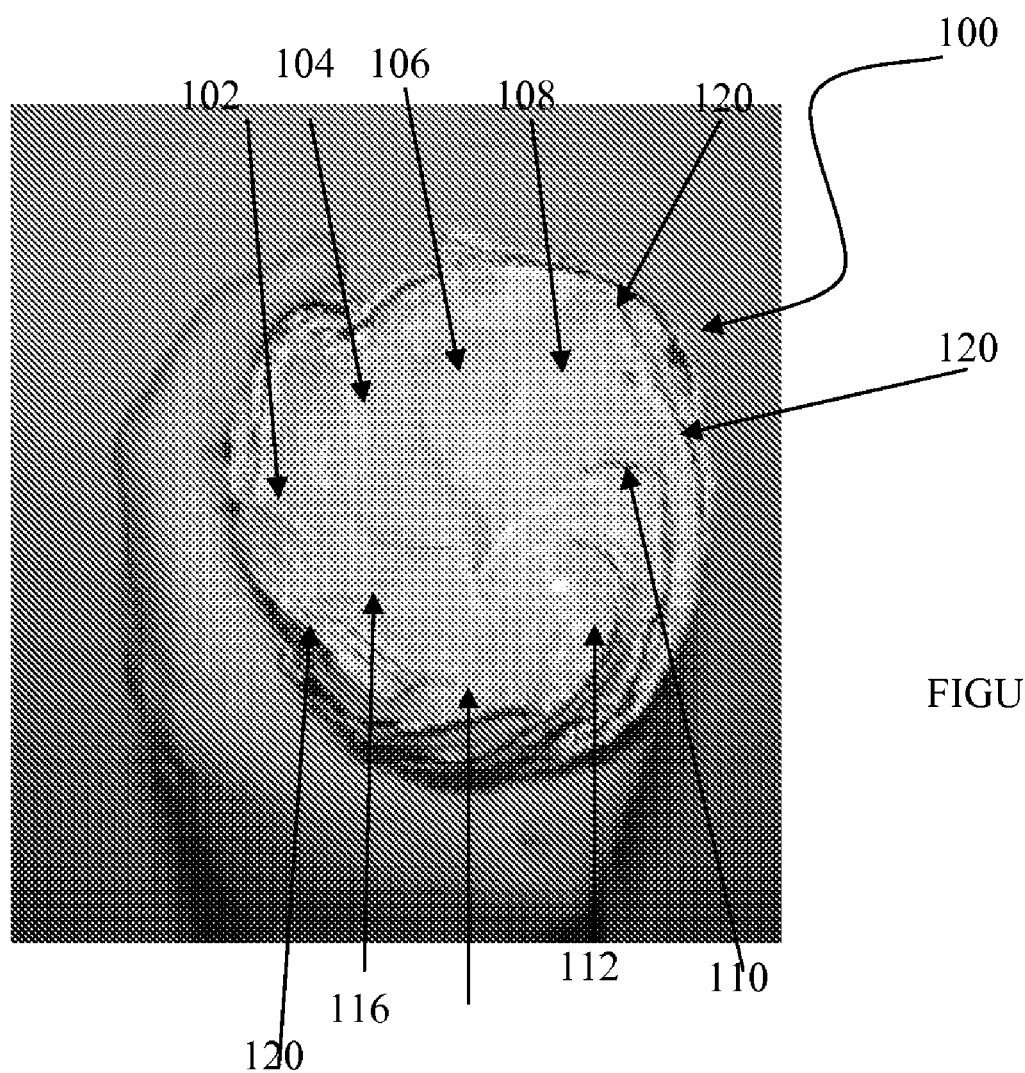
Figure 22C:
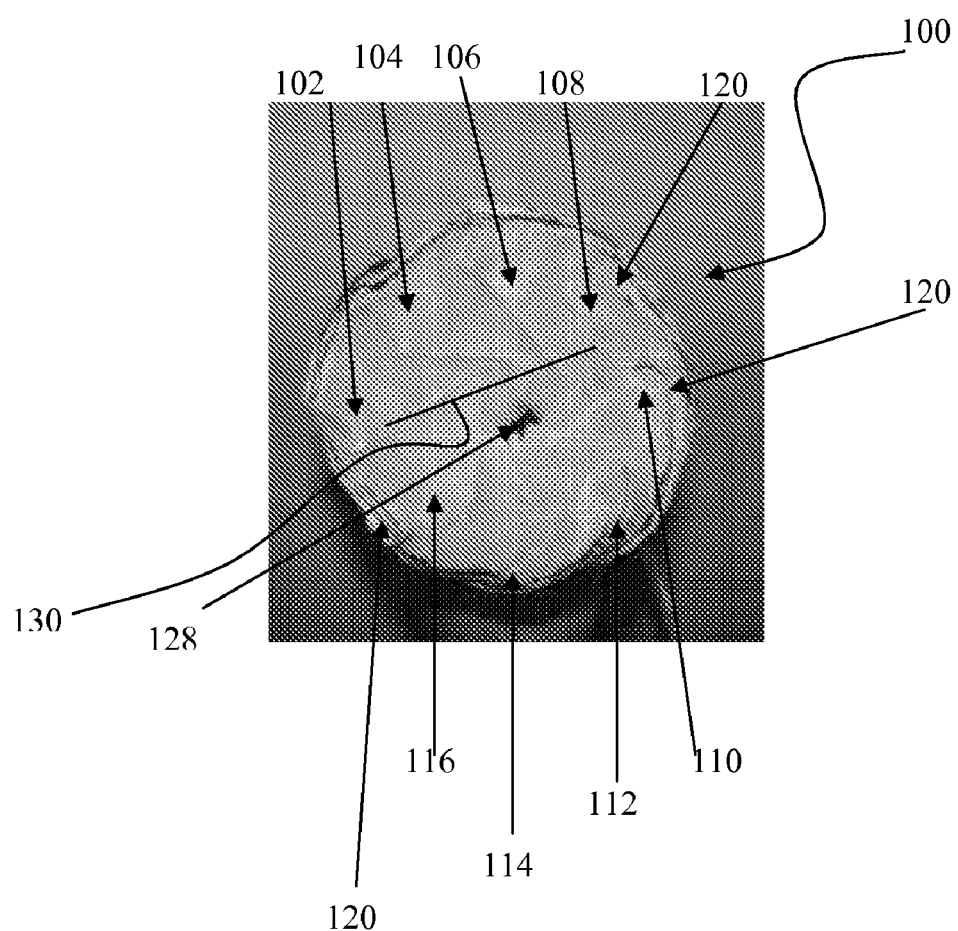

FIGS. 22A, 22B and 22C are top view images that illustrate a device according to one embodiment of the present invention expanding from collapsed configuration in FIG. 22A to a partially open configuration in FIG. 22B to an open configuration in FIG. 22C. FIGS. 22A, 22B and 22C include the overlapped membranes 102-116 in a partial overlapping arrangement. Each of the overlapped membranes 102-116 include one or more resilient members 120 incorporated therein. The overlapping arrangement and the orientation of the attached outer edge and the free inner edge create an epicardium chamber. The size of the epicardium chamber depends on the degree of overlap of the overlapped membranes 102-116. As seen in FIG. 22A the collapsed state results in a greater degree of overlap of the overlapped membranes 102-116 and a smaller epicardium chamber than in the expanded FIG. 22B and FIG. 22C. The expanded device 100 in FIG. 22C has overlapped membranes 102-116 and maintains an epicardium chamber 130 that is not obliterated and the apical aperture 128 remaining visible at the apical end (not shown). In addition, the bladders positioned within the overlapped membranes 102-116 may protrude inward, but still do not obliterate the epicardium chamber 130. The free inner edge on the overlapped membranes 102-116 permits the overlapped membranes 102-116 to collapse upon each other for implanting the device through a small incision in the body. The resilient members result in the device 100 provide for the opening of the device 100 in a twisting sort of manner.

Another embodiment of the present invention includes a direct compression cardiac device where the resilient inner panel, the expandable outer panel or both are connected to a source to allow inflating and deflating. Other embodiments of the present invention include a direct compression cardiac device where the resilient inner panel, the expandable outer panel or both are connected to a source to allow inflating and deflating, a mechanical compression device is tightened, gated with the ECG or cardiac contraction.

Figure 23A:
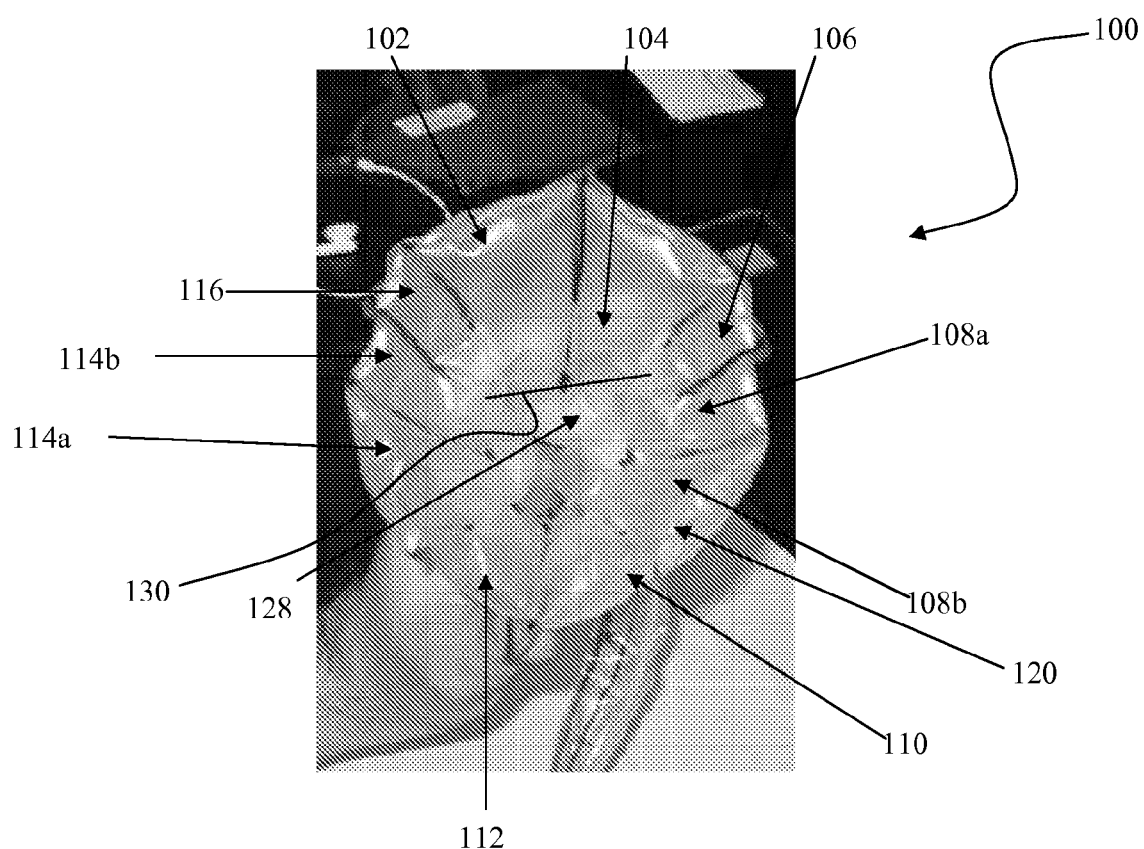
FIGS. 23A and 23B are images that illustrate a device according to yet another embodiment of the present invention.
Figure 23B:
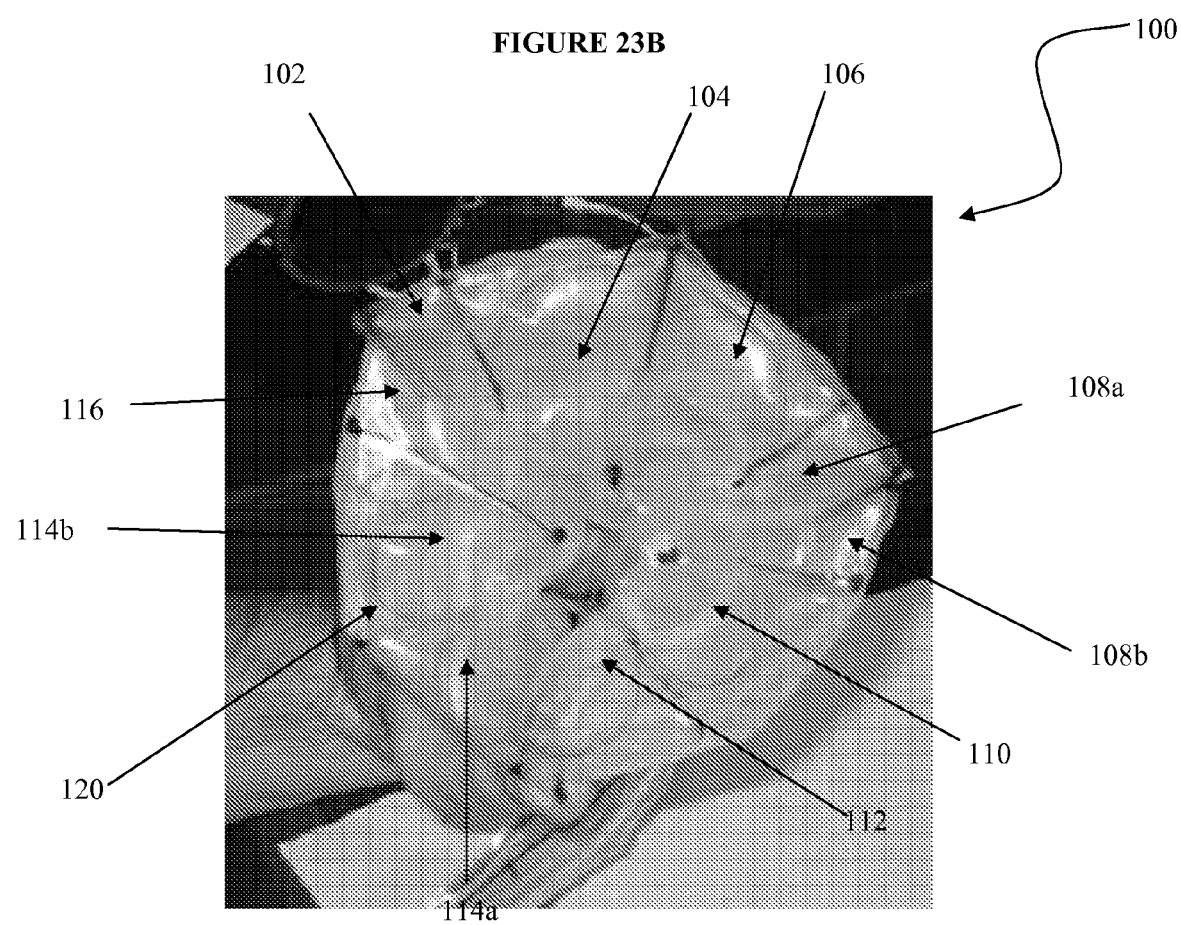

FIGS. 23A and 23B illustrate a direct compression cardiac device of the present invention having inner segmented polyurethane chambers 102, 104, 106, 108a, 108b, 110, 112, 114a, 114b and 116 and one external bladder (not shown). Each of the inner segmented polyurethane chambers 102-116 includes one or more resilient members 120 incorporated into each of the inner segmented polyurethane chambers 102-116 and the inner surface of the inner segmented polyurethane chambers 102-116 are relatively free to move inward to contact the epicardium (not shown) of the heart (not shown). The presence of both inner segmented polyurethane chambers 102-116 and an external bladder (not shown) allow more precise control of the structure of the device and in turn the structure of the heart. FIG. 23A is an image that illustrates a device with the i inner segmented polyurethane chambers 102, 104, 106, 108a, 108b, 110, 112, 114a, 114b and 116 fully inflated and the external chamber (not shown) deflated. This orientation of the device 100 controls the end-diastolic volume of the heart (not shown). FIG. 23B is an image that illustrates a device with the inner segmented polyurethane chambers 102, 104, 105, 108a, 108b, 110, 112, 114a, 114b and 116 and the external chambers (not shown) fully inflated. This orientation of the device 100 controls the end-systolic volume of the heart (not shown), making the device 100 an active device.

One embodiment of the present invention includes a resilient inner panel and an expandable outer panel to allow passive and active components. The passive portion allows the chamber volume to be modulated with or gated relative to the ECG or cardiac contraction. The active portion allows other component to be activated, modulated or gated relative to the ECG or cardiac contraction.

Another embodiment of the present invention provides a pneumatically controlled direct compression cardiac device that directly modulates the end-diastolic volume but not the end-systolic volume. For the passive component, the chambers and the pneumatic lines could be small (relative to the active component) because a fast temporal response is not necessary. Also, the end-diastolic volume adjustment could be via a transcutaneous, transient needle access as opposed to a continuous transcutaneous line. Small access lines and transient access are each (and together) beneficial for minimizing infection.

The present invention provides a method of individually modulating the heart volumes by positioning a direct compression cardiac device about at least a portion of a heart and optionally modulating the resistance supplied by the resilient inner panel to the heart to control the end-diastolic heart volume, the resistance supplied by the expandable outer panel to the heart to control the end-systolic heart volume or both. The direct compression cardiac device includes a resilient inner panel in contact with at least a portion of the heart periphery and at least partially surrounded by an expandable outer panel.

The resilient inner panel includes two or more at least partially overlapped membranes, e.g., 3, 4, 5, 6, 7, 8, 9, 10, 11, 12, 13, 14, 15, 16, 17, 18, 19, 20 or more. The portion of each membrane that is overlapped may be at the top, middle and/or bottom or a combination thereof. The degree of overlap may be from 1% to 99% overlap depending on the desired affect and number of membranes used. In addition, the overlap does not need to be uniformed between the membranes (e.g., some membranes may have more overlap at different points on one membrane than another membrane) and/or different overlaps between membranes (e.g., specific areas of the device may have a greater degree of overlap to increase resistance in that region. Furthermore, the resilient inner panel may include one or more inflatable bladders positioned about the two or more at least partially overlapped membranes. The number of bladders will be dictated by the desired effect on the heart. For example, there may be 1, 2, 3, 4, 5, 6, 7, 8 or more bladders per membrane or there may be 1 bladder for multiple membranes. One example includes 8 membranes and 8 bladders arranged to provide resistance to the periphery of the heart.

Another embodiment of the present invention provides a device to separately modulate the mechanics of systole and diastole. The device includes two-components, an inner, passive shape modulator surrounded by an active outer surround. The passive shape modulator includes multiple pneumatic chambers that when pressurized induce a heart like shape. By gradually filling the passive shape modulator chambers, the diastolic volume can be reduced. The active outer surround is like a pneumatic belt that when inflated during systole, rapidly increases the pressure in the inner passive shape modulator component by pushing on its pneumatic chambers. The active outer surround pressure in turn is transferred through the passive shape modulator to the heart surface.

Figure 24:
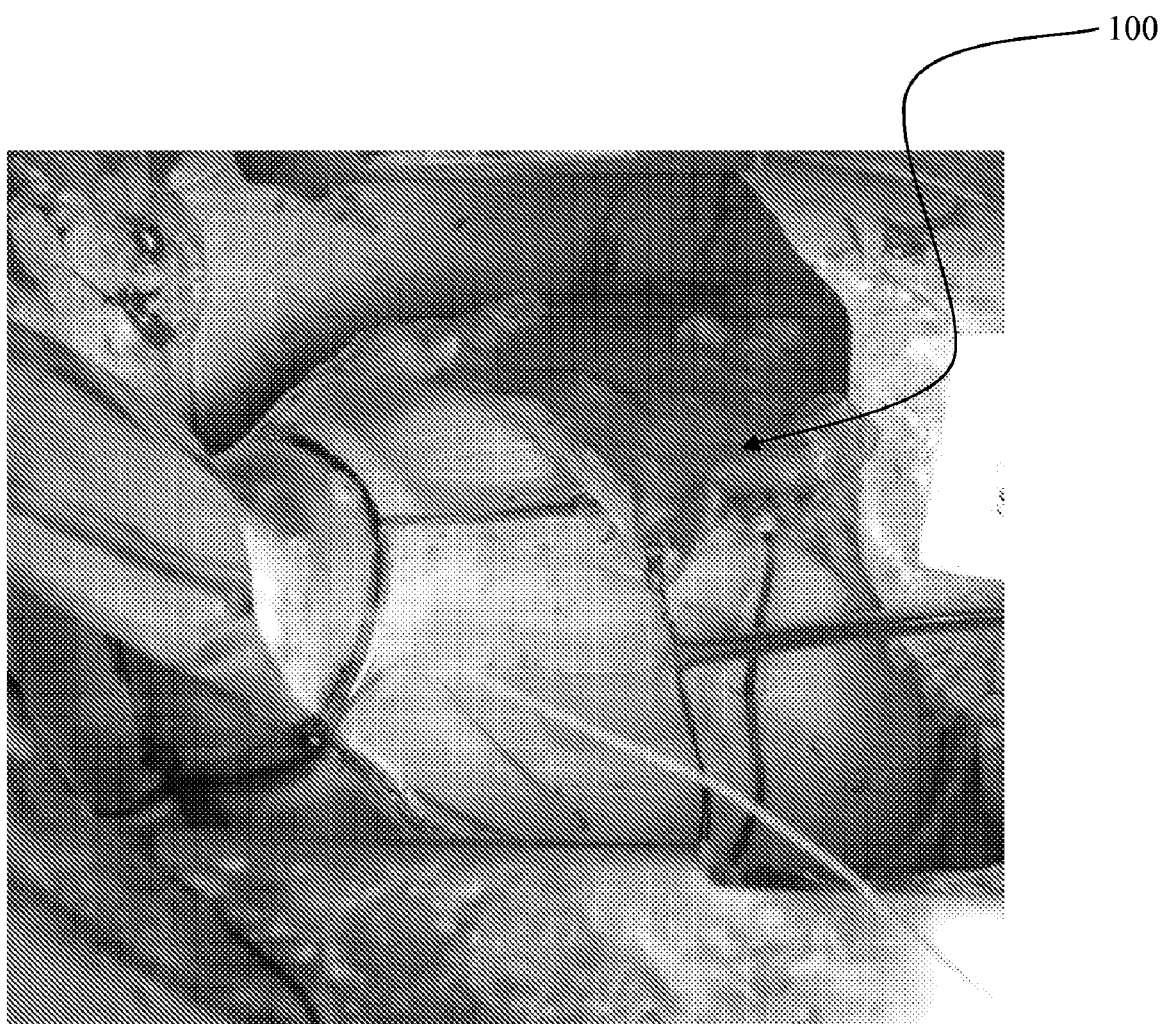
FIG. 24 is an image of one embodiment of the present invention that separately modulate EDV and ESV.

FIG. 24 illustrates one embodiment of the present invention implanted in a sheep. End diastolic volume could be reduced and/or modulated by filling the passive shape modulator and end-systolic volume could be reduced/modulated by pressurizing the active outer surround in synchrony with the ECG.

FIG. 24 is an image of one embodiment of the present invention that provides a two component device to separately modulate EDV and ESV. Implanted 100 and viewed through a sternotomy. The outer component, or active jacket active outer surround, has one pneumatic chamber that encircles the heart at the equatorial region (i.e., the basal third if the heart was divided into thirds transverse to the apex-base axis). The active outer surround is pressurized in synchrony with the ECG via Q-wave triggering. The inner component, or passive shape modulator, can be seen, slightly, through the polyurethane active outer surround. For example, the passive shape modulator is very similar to the one-component device of FIG. 1; except with 8 chambers instead of 6 chambers. By filling the passive shape modulator, the overall volume of the heart can be decreased. By pushing on the upper part of the passive shape modulator, the pressure in the passive shape modulator chambers is rapidly increased when the active outer surround is pressurized.

This embodiment may also be was implanted via a sternotomy. The two component device was twice as bulky, but still collapsible into about a 1.5 inch diameter tube. The problem with our attempt at minimally invasive implantation was that the device had insufficient internal structure to expand the device once it was deployed into the cavity. There is not enough space in the pericardial sac to deploy the entire device and let it expand, rather it needs to begin expanding as it is deployed. This embodiment of the present invention provides an internal wire frame as seen in FIG. 24 to reside between the two components.

Figure 25A:
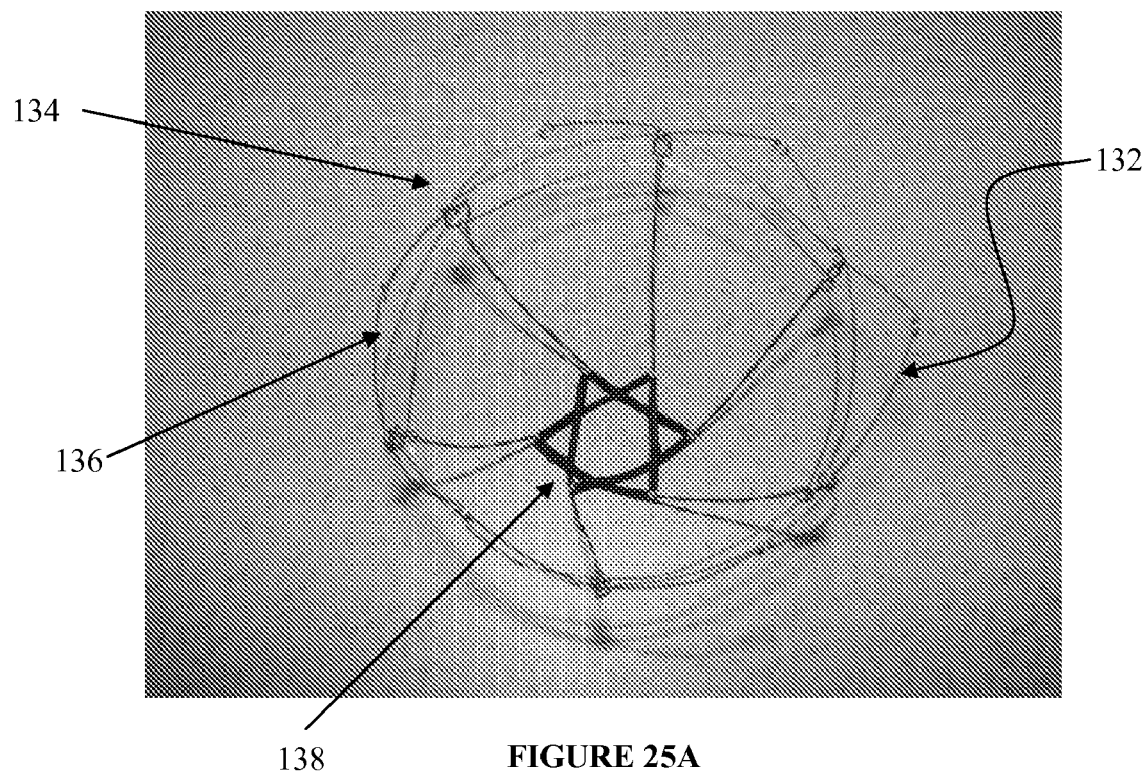
FIGS. 25A and 25B are images of the wire frame that stores energy to be released during deployment/expansion, top and side respectively.
Figure 25B:
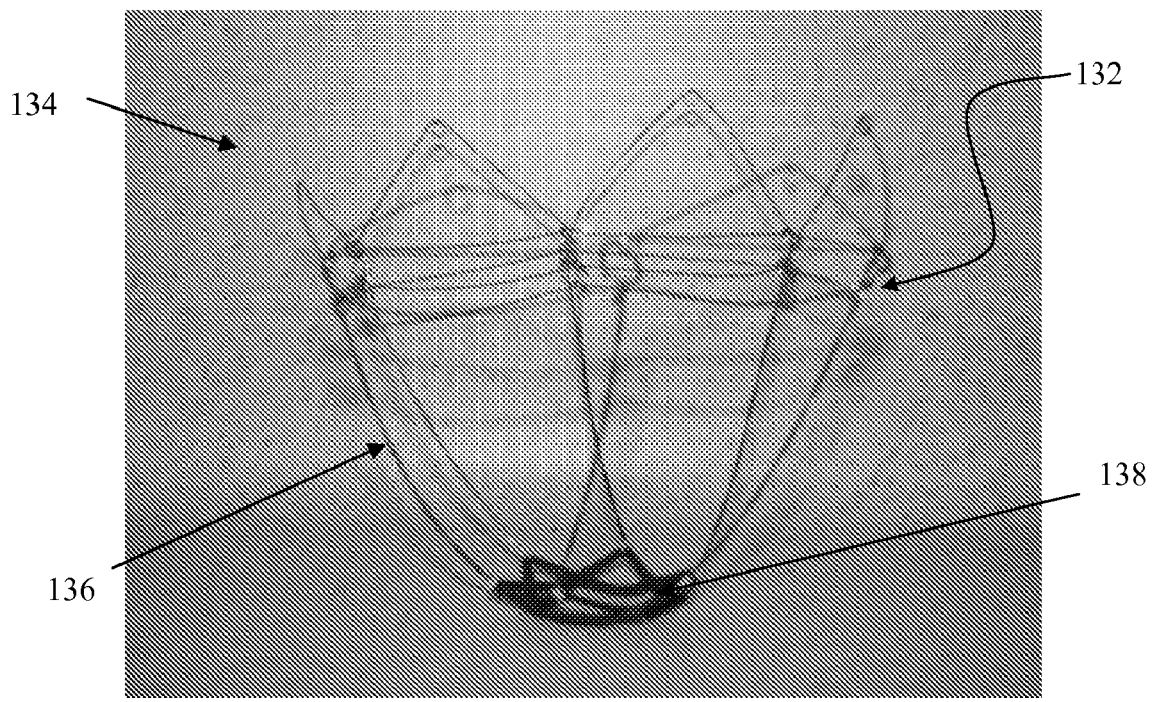

FIG. 25A is a top view and FIG. 25B is a side view of a wire frame 132 that stores energy to be released during deployment/expansion. The shape and size of the wire frame 132 may be adjusted so that it may fit hearts of different sizes from infant to adult, large to small, enlarged by diseased and so forth. In addition, shape of the wire frame 132 at the top may be different from region to region and the different regions may be constructed from similar or different materials to customize the affect as needed. The wire frame 132 includes a top basal rig 134 that collapses by overlapping the six segments and stores energy in twisted wire pairs 136. The bottom part 138 collapses via twisting of the apex, and stores energy in the torsion of the twisted wire pairs 136. The top opens separately from the bottom part 138 because the twisted wire pairs 136 release their energy even while the apical part is twisted. A series of images of the expanding frame is shown in FIG. 26.

Figure 26A:
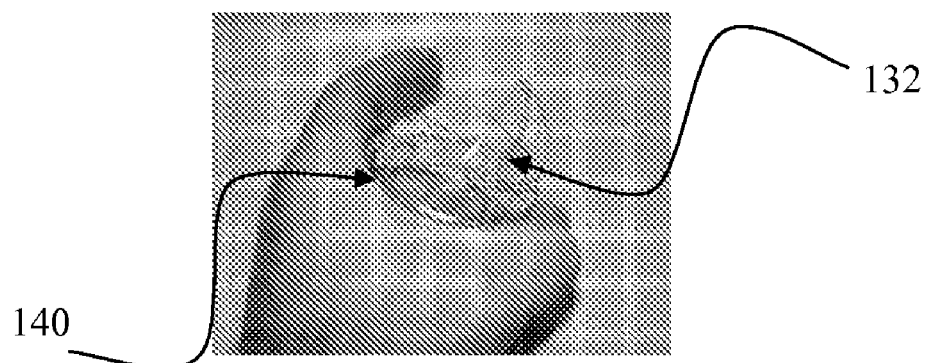
FIGS. 26A-26D are a series of images illustrating one embodiment of the present invention as if deployed through a tube.
Figure 26B:
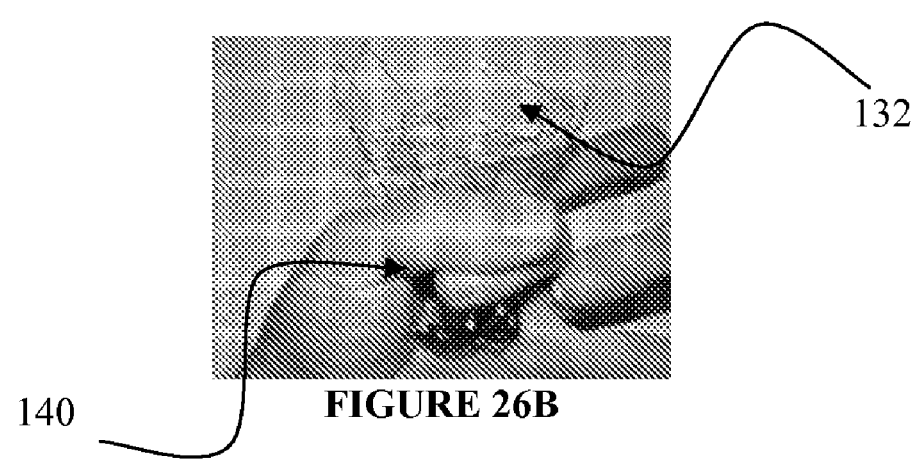
Figure 26C:
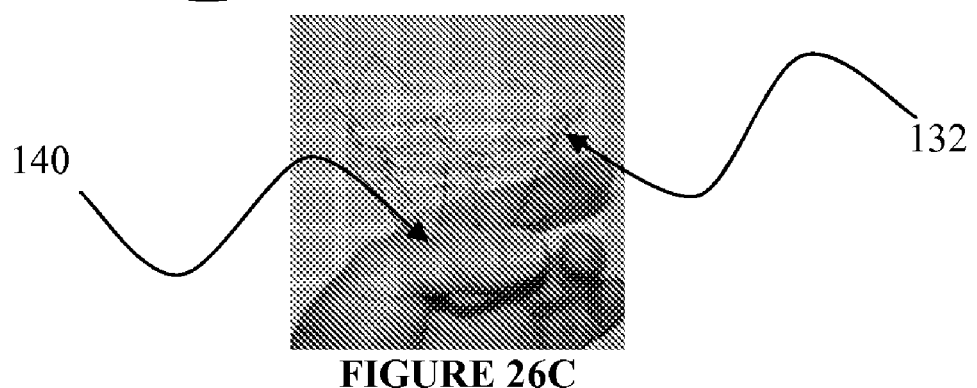
Figure 26D:
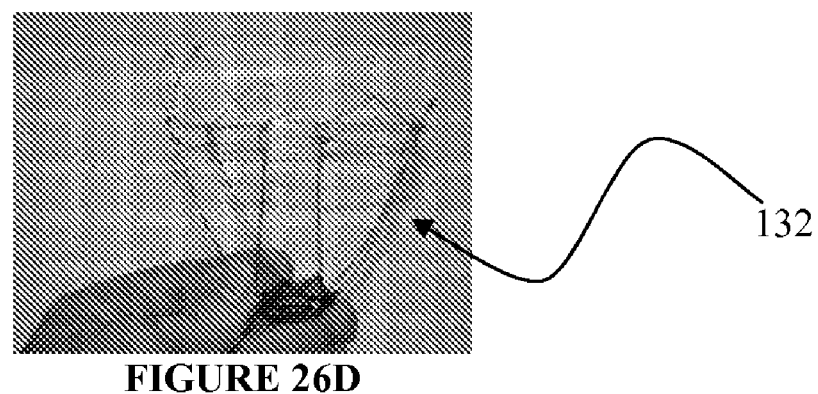

FIG. 26A to 26D are images that illustrate the wire frame 132 as if deployed through a simulated orifice to demonstrate the implantation of the device through an incision. In FIG. 26A the basal portion expands even while the apical portion is still collapsed. In order to pass through and be deployed through a tube into the pericardial space, the frame goes from cylinder shape as in FIG. 26B, to fluted shape as in FIG. 26C, to cup shape in FIG. 26D, as it is extruded out of the tube. The present invention provides an insert that may be positioned between the resilient inner panel and inflatable outer panel, about the resilient inner panel or the inflatable outer panel, both or a combination thereof. The one or more resilient members may be in the form of a collapsible wire frame that can be compressed for insertion and expands to a basic cup shape when inserted into a pericardial space. The collapsible wire frame may be made from numerous wires arranged to allow collapse and expansion while providing the resistance required.

A device driver may be used to pressurize the active outer surround in synchrony with the ECG. For example, a custom circuit with Q wave triggering may be used to pressurize the active outer surround in synchrony with the ECG. The relays control solenoid valves on the pressure reservoir and vacuum line. Basically, when triggered by the Q-wave the pressure valve is opened and the vacuum valve is closed for an adjustable time delay that is manually determined to roughly correspond with relaxation. After the delay, the pressure valve is closed and the vacuum valve is opened until the next Q-wave trigger. Aortic balloon pumps are counter pulsation whereas the proposed device is direct pulsation.

Another embodiment of the present invention provide a device that is optimized for treating acute heart failure wherewith circulatory assist is needed urgently to restore blood flow and restore normal motion to the heart (i.e., eliminate or significantly reduce dyskinesis so to prevent myocyte and ECM remodeling). For acute heart failure, remodeling has not yet occurred, and thus reverse remodeling is not needed. For CHF, however, the heart shape is grossly abnormal and there is a need to modulate systolic and diastolic wall stress and/or strain to better understand the mechanisms of and thus treatments for CHF.

The overlapped membranes may be made in-part or entirely from an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

The one or more inflatable bladders may be constructed from an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

The one or more inflatable bladders may contain a gas, a liquid, a gel or a combination thereof to provide resistance. The contents of the bladders may be added before, during and/or after implantation. In addition, the contents may be adjusted post implantation to regulate the pressure as necessary. Alternatively, the bladders may be connected (independently or as a group) to a source to provide resistance to the heart. Both the static bladders (e.g., those filled with a fixed volume and sealed but may be changed as needed) and the active bladders (e.g., those connected to a source to actively supply pressure) may be adjusted to control the resistance to the periphery of the heart through inflation and deflation of the one or more inflatable bladders connected to a source.

The source to supply the inflation and deflation of the one or more inflatable bladders will depend on the content of the bladder. For example, a pneumatic device, cylinder, pump, reservoir and so forth may be used to supply air, nitrogen, oxygen, hydrogen, helium, argon and any other gas. A pressurized cylinder, pump, reservoir and so forth may be used to supply liquids and gels. In addition, a mechanical compression device may be added to the resilient inner panel for increasing the pressure applied to the heart, e.g., a lap band. The mechanical compression device may be adjusted to control the restriction placed on the resilient inner panel and in turn resistance applied to the heart. This allows the resistance to be adjusted easily as the condition changes.

The direct compression cardiac device also includes one or more resilient members positioned about the resilient inner panel. The resilient members may be used to supply resistance to the heart either with or without the addition of bladders. The number, size, length, diameter, cross-section, profile, width, composition and other physical characteristics may be changes as necessary to produce the desired resistance. The one or more resilient members may be individually a metal, an alloy, a memory metal, a composite, a polymer, a plastic or a combination thereof. One specific embodiment of the present invention includes memory metals or metal alloys, e.g., zinc, aluminium, copper, aluminium, nickel, and titanium; copper-zinc-aluminium, copper-aluminium-nickel, and nickel-titanium (NiTi) alloys and combinations thereof. Other examples include: Ag—Cd at differing percentages of Cd (e.g., 44-49%); Au—Cd at differing percentages of Cd (e.g., 46.5-50%); Cu—Al—Ni at differing percentages of Al (e.g., 14-14.5 wt. %) and at differing percentages of Ni (e.g., 3-4.5 wt. %); Cu—Sn at differing percentages of Sn (e.g., 15%); Cu—Zn at differing percentages of Zn (e.g., 38.5-41.5 wt. %); Cu—Zn—X (X=Si, Sn, Al) at differing percentages of X (e.g., 0-10 wt. %); In—Ti at differing percentages of Ti (e.g., 18-23%); Ni—Al at differing percentages of Al (e.g., 36-38%); Ni—Ti at differing percentages of Ni (e.g., 49-51%); Fe—Pt at differing percentages of Pt (e.g., 25%); Mn—Cu at differing percentages of Cu (e.g., 5-35%); Fe—Mn—Si; Pt alloys; Co—Ni—Al and Co—Ni—Ga. Furthermore, the position and the method of attaching the resilient members about the resilient inner panel may be altered as necessary to provide resistance.

The expandable outer panel contacts and at least partially surrounds the resilient inner panel positioned about at least a portion of the heart periphery to supply resistance to control the end-systolic heart volume or both. The expandable outer panel may also have one or more (overlapping or non-overlapping) membranes, e.g., 3, 4, 5, 6, 7, 8, 9, 10, 11, 12, 13, 14, 15, 16, 17, 18, 19, 20 or more. Furthermore, the expandable outer panel may include one or more inflatable bladders. The number of bladders will be dictated by the desired effect on the heart. For example, there may be 1, 2, 3, 4, 5 or more inflatable bladders per membrane or there may be one inflatable bladder for multiple membranes. The inflatable bladders may be connected to each other and/or to a source to inflate and deflate the expandable outer panel and apply pressure to the heart. The expandable outer panel may also include one or more fluid connections (e.g., an inlet port and an outlet port) to inflate with positive pressure during systole and deflate with suction during diastole. The one or more expandable outer panel may be constructed from an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

In addition, a mechanical compression device may be added to the expandable outer panel for increasing the pressure applied to the heart, e.g., a lap band. The mechanical compression device may be adjusted to control the restriction and in turn the resistance applied to the heart. This allows the resistance to be adjusted easily as the condition changes.

The present invention may also include one or more sensors, one or more electrodes, one or more conductive elements, one or more monitoring devices, one or more transmitters, one or more receivers, one or more actuators, or a combination thereof in contact with the direct compression cardiac device. One or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof may be implanted, coated or disseminated The present invention may be used to create the proper end-systolic shape of the heart, end-diastolic shape of the heart or both. The contoured supports can be used to provide an expanded curvature similar to the proper end-systolic shape of the heart and/or the proper end-diastolic shape of the heart. A direct cardiac compression device applies force to the exterior, epicardial boundary of the heart to restrict inflow and modulate right flow versus left flow through the heart to promote contraction strain patterns on a diseased or damaged heart to reduce dyskinetic or hypokinetic motions.

In addition the present invention provides a kit including a direct cardiac compression heart assist device having a resilient inner panel and an inflatable outer panel. The resilient inner panel contacts a heart periphery and includes two or more at least partially overlapped membranes in contact with one or more resilient members. The overlapped membranes are contoured to provide curvatures generally in the shape of the heart. The resilient inner panel supplies resistance to the movement of the heart to affect the end-diastolic heart volume. The inflatable outer pane includes one or more inflatable membranes positioned at least partially around the resilient inner panel and includes one or more inflatable membranes to provide resistance to the movement of the heart to affect the end-systolic heart volume. The inflatable outer panel also includes one or more fluid connections in communication for inflation and deflation. Optionally, the kit may include one, a set or more than one inflatable bladder for insertion into the overlapped membranes.

Generally, when a material is implanted in the body, the body recognizes the presence of the foreign material and triggers an immune defense system to eject and destroy the foreign material. This results in edema, inflammation of the surrounding tissue and biodegradation of the implanted material. As a result the biomedical implantable material must be carefully selected. Examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments made of a biocompatible, biostable, implantable polyamide, polyimide, polyester, polypropylene, polyurethane, etc.

The incidence of infection associated with medical device implantation is often life threatening, e.g., *entercoccus, pseudomonas auerignosa, staphylococcus* and *staphylococcus epidermis* infections. The present invention may include bioactive layers or coatings to prevent or reduce infections. For example, bioactive agents may be implanted, coated or disseminated from the present invention and include antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof. Antimicrobial agents include but are not limited to benzalkoniumchloride, chlorhexidine dihydrochloride, dodecarbonium chloride and silver sufadiazine. Generally, the amount of antimicrobial agent required depends upon the agent; however, concentrations may range from 0.0001% to 5.0%.

In addition, some embodiments of the present invention may have leads, electrodes or electrical connections incorporated into the device. When present, they may be made from noble metals (e.g., gold, platinum, rhodium and their alloys) or stainless steel. In addition, ordinary pacemaker leads and defibrillation leads could be also incorporated into the present invention to provide cardiac pacing or defibrillation.

Although the present invention and its advantages have been described in detail, it should be understood that various changes, substitutions and alterations can be made herein without departing from the spirit and scope of the invention as defined by the following claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

American Heart Association (2003). Heart Disease and Stroke Statistics-2004 Update. Dallas, Tx: American Heart Association.

Anstadt, M. P., Schulte-Eistrup, S. A., Motomura, T., Soltero, E. R., Takano, T., Mikati, I. A., Nonaka, K., Joglar, F., Nose, Y. (2002). Non-blood contacting biventricular support for severe heart failure. Ann Thorac Surg 73: 556-62.

Artrip, J. H., Yi, G. H., Levin, H. R., Burkhoff, D., Wang, J. (1999). Physiological and hemodynamic evaluation of nonuniform direct cardiac compression. Circulation 100 (suppl II): 236-43.

Bax, J. J., Poldermans, D., Allhendy, A., Boersma, E., Rahimtoola, S. H. (2001) Sensitivity, specificity, and predictive accuracy of various noninvasive techniques for detecting hibernating myocardium. Curr Probl Cardiol 26: 141-186.

Bruckner, B. A., Stetson, S. J., Perez-Verdia, A., Youker, K. A., Radovancevic, B., Koerner, M. M., Entman, M. L., Frazier, O. H., Noon, G. P., Torre-Amione, G. (2001) Regression of fibrosis and hypertrophy in failing myocardium following mechanical circulatory support. J Heart Lung Transplant 20: 457-464.

Cooley, D. A., and Frazier, O. H. (2000). The past 50 years of cardiovascular surgery. Circulation 102: IV88-93.

Cooper, G. (1987). Cardiocyte adaptation to chronically altered load. Annu. Rev. Physiol. 49: 501-518.

Dipla, K., Mattiello, J. A., Jeevanandam, V., Houser, S. R., Margulies, K. B. (1998) Myocyte recovery after mechanical circulatory support in humans with end-stage heart failure. Circulation 97: 2316-2322.

Feldman, A. M., Weinberg, E. O., Ray, P. E., and Lorell, B. H. (1993). Selective changes in cardiac gene expression during compensated hypertrophy and the transition to cardiac decompensation in rats with chronic aortic banding. Circ. Res. 73: 184-192.

Figueredo, V., and Camacho, S. (1994). Basic mechanisms of myocardial dysfunction: Cellular pathophysiology of heart failure. Curr. Op. Cardiol. 9: 272-279.

Gerdes, A. M., and Capasso, J. M., (1995). Structural remodeling and mechanical dysfunction of cardiac myocytes in heart failure. J. Mol. Cell. Cardiol. 27: 849-856.

Gheorghiad, M., and Bonow, R. O., (1998). Chronic heart failure in the united states: a manifestation of coronary artery disease. Circulation 97:282-9.

Goldstein, D. J., Oz, M. C., Rose, E. A. (1998) Medical progress: implantable left ventricular assist devices. N Engl J Med 339(21): 1522-1533.

Grossman, W. (1980). Cardiac hypertrophy: Useful adaptation or pathologic process? Am. J. Med. 69: 576-583.

Guccione, J. M., Moonly, S. M., Moustakidis, P., Costa, K. D., Moulton, M. J., Ratcliffe, M. B., Pasque, M. K., (2001). Mechanism underlying mechanical dysfunction in the boarder zone of left ventricular aneurysm: a finite element model study. Ann. Thorac. Surg. 71:654-62.

Gwathmey, J. K., Copelas, L., MacKinnon, R., Schoen, F. J., Feldman, M. D., Gorssman, W., and Morgan, J. P. (1987). Abnormal intracellular calcium handling in myocardium from patients with end-stage heart failure. Circ. Res. 61: 70-76.

Heerdt, P. M., Holmes, J. W., Cai, B., Barbone, A., Madigan, J. D., Reiken, S., Lee, D. L., Oz, M. C., Marks, A. R., Burkhoff, D. (2000) Classic unloading by left ventricular assist device reverses contractile dysfunction and alters gene expression in end-stage heart failure. Circulation 102: 2713-2719.

Helman, D. N., Rose, E. A. (2000) History of mechanical circulatory support. Progress in Cardiovascular Diseases 43(1): 1-4.

Hewson, C. E. (1962), Inflatable heart massager. U.S. Pat. No. 3,034,501.

Hons, J. K. F. and Yacoub, M. H. (2003), Bridge to recovery with the use of left ventricular assist device and clenbuterol. Ann. Thorac. Surg. 75:S36-41.

Hosenpud, J. D., Bennett, L. E., Keck, B. M., Boucek, M. M., Novick, R. J., (2000). The registry of the international society for heart and lung transplantation: seventeenth official report. J Heart Lung Transplant 19: 909-31.

Humphrey, J. D., (2002). Cardiovascular Solid Mechanics: Cells, Tissues, and Organs. New York: Springer. p. 166-178, 674.

Humphrey J D, Rajagopal K R (2003) A constrained mixture model of arterial adaptations to a sustained step change in blood flows. Biomech. Model Mechanobiol. 2:107-126.

Kajstura, J., Zhang, X., Liu, Y., Szoke, E., Cheng, W., Olivetti, G., Hintze, T., and Anversa, P. (1995). The cellular basis of pacing-induced dilated cardiomyopathy. Myocyte cell loss and myoyte cellular reactive hypertrophy. Circulation 92: 2306-2317.

Karvarana, M. N., Helman, D. N., Williams, M. R., Barbone, A., Sanchez, J. A., Rose, E. A., Oz, M. C., Milbocker, M., Kung, R. T. V., (2001). Circulatory support with a direct cardiac compression device: a less invasive approach with the AbioBooster device. J Thorac Cardiovasc Surg 122: 786-787.

Kawaguchi, O., Goto, Y., Futaki, S., Ohgoshi, Y., Yaku, H., Suga, H. (1992). Mechanical enhancement of myocardial oxygen saving by synchronized dynamic left ventricular compression. J Thorac Cardiovasc Surg 103:573-81.

Kherani. A. R., Maybaum, S., Oz, M. C. (2004) Ventricular assist devices as a bridge to transplant or recovery. Cardiol 101:93-103.

Komuro, I., and Yazaki, Y. (1993). Control of cardiac gene expression by mechanical stress. Ann. Rev. Physiol. 55: 55-75.

Kung and Rosenberg (1999). Heart booster: a pericardial support device. Annals of Thoracic Surgery 68:764-7.

Marian, A., Zhao, G., Seta, Y., Roberts, R., and Yu, Q. (1997). Expression of a mutant (Arg92Gln) human cardiac troponin T, known to cause hypertrophic cardiomyopathy, impairs adult cardiac myocyte contractility. Circ. Res. 81: 76-85.

Omens, J. H. (1998). Stress and strain as regulators of myocardial growth. Prog. Biophys. Molec. Biol. 69: 559-572.

Oz, M. C., Artrip, J. H., Burkhoff, D., (2002). Direct cardiac compression devices. Heart Lung Transplant 21: 1049-1055.

Packer, M., Coats, A J., Fowler, M B., Katus, H A., Krum, H., Mohacsi, P., Rouleau, J L., Tendera, M., Castaigne, A., Roecker, E B., Schultz, M K., DeMets, D L. Carvedilol Prospective Randomized Cumulative Survival Study Group. (2001). Effect of carvedilol on survival in severe chronic heart failure. N Engl J Med 344(22): 1651-8.

Parravicini (1985). U.S. Pat. No. 4,536,893.

Rose, E. A., Gelijns, A. C., Moskowitz, A. J., Heitjan, D. F., Stevenson, L. W., Dembitsky, W., Long, J. W., Ascheim, D. D., Tierney, A. R., Levitan, R. G., Watson, J. T., Ronan, N. S., Meier, P. (2001). Long-term use of left ventricular assist device for end-stage heart failure. N Engl J Med 345(20): 1435-1443.

Sabbah, H., and Sharov, V. (1998). Apoptosis in heart failure. Prog. Cardiovasc. Dis. 40: 549-562.

Sadoshima, J., and Izumo, S. (1997). The cellular and molecular response of cardiac myocytes to mechanical stress. Ann. Rev. Physiol. 59: 551-571.

SOLVD Investigators (1991). Effect of enalapril on survival in patients with reduced left ventricular ejection fractions and congestive heart failure. N Engl J Med 325: 293-302.

Taber L A (2001) Biomechanics of cardiovascular development. Ann. Rev. Biomed Engr. 3:1-25.

Torre-Amione, G., Stetson, S. J., Youker, K. A., Durand, J. B., Radovancevic, B., Delgado, R. M., Frazier, O. H., Entman, M. L., Noon, G. P. (1999) Decreased expression of tumor necrosis factor-alpha in failing human myocardium after mechanical circulatory support: A potential mechanism for cardiac recovery. Circulation 100: 1189-1193.

Vineberg, A. (1958). Cardiac Resuscitation Device. U.S. Pat. No. 2,826,193.

Weber, K. T., Brilla, C. G., and Janicki, J. S. (1993). Myocardial fibrosis: Functional significance and regulatory factors. Cardiovasc. Res. 27: 341-348.

Williams, M. R., Artrip, J. H. (2001). Direct cardiac compression for cardiogenic shock with the CardioSupport System. Ann Thorac Surg 71: S188-9.

Wolff, M. R., Buck, S. H., Stoker, S. W., Greaser, M. L., Mentzer, R. M. (1996) Myofibrillar calcium sensitivity of isometric tension is increased in human dilated cardiomyopathies: Role of altered beta-adrenergically mediated protein phosphorylation. J Clin Invest 98: 167-176.

Zafeiridis, A., Jeevanandam, V., Houser, S. R., Margulies, K. B. (1998) Regression of cellular hypertrophy after left ventricular assist device support. Circulation 98: 656-662.

What is claimed is:

1. A method of individually modulating the heart volume comprising the steps of:

positioning a direct compression cardiac device about at least a portion of a heart, wherein the direct compression cardiac device comprising a resilient inner panel in contact with at least a portion of the heart periphery and at least partially surrounded by an expandable outer panel, wherein the resilient inner panel has a selectively inflatable end-systolic heart shape and at least one inflatable bladder with a heart shaped contoured to surround at least a portion of a heart to provide curvatures similar to the proper shape of the heart when pressurized to compress the heart during contraction without inverting or significantly perturbing the curvatures of the heart, one or more fluid connections in communication with the expandable outer panel and resilient inner panel for pressurization and depressurization;

pressurizing the direct compression cardiac device to compress the heart during contraction without inverting or significantly perturbing the curvatures of the heart; and modulating the resistance supplied by the inner panel to the heart to control the end-diastolic heart volume, the resistance supplied by the expandable outer panel to the heart to control the end-systolic heart volume or both.

2. The method of claim 1, further comprising the step of controlling actively the resistance to the periphery of the heart through inflation and deflation of the one or more inflatable bladders connected to a source.

3. The method of claim 1, wherein the direct compression cardiac device further comprises two or more at least partially overlapped membranes connected to form a continuous outer edge and one or more resilient members in contact with each of the about eight at least partially overlapped membranes.

4. The method of claim 1, wherein the resilient inner panel further comprises a mechanical compression device for increasing the pressure applied to the heart.

5. The method of claim 4, further comprising modulating the resistance on the resilient inner panel with an internal band.

6. The method of claim 1, wherein the resilient inner panel, the inflatable outer panel or both comprises an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

7. The method of claim 1, further comprising one or more resilient members positioned about the resilient inner panel.

8. The method of claim 7, wherein the one or more resilient members comprise individually a metal, an alloy, a memory metal, a composite, a polymer, a plastic or a combination thereof.

9. The method of claim 1, further comprising one or more sensors, one or more electrodes to provide pacing stimuli to the heart, one or more electrodes to provide an electrical shock to the heart for defibrillation, one or more electrodes to provide an electrical stimuli to the heart, or a combination thereof in contact with the direct compression cardiac device.

10. The method of claim 1, further comprising implanting, coating or disseminating one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

11. A method of remodeling the shape of a heart a patient by controlling the end-diastolic heart volume and the end-systolic heart volume comprising the steps of:

determining the shape of the heart of the patient;

positioning a direct compression cardiac device about at least a portion of a heart, the direct compression cardiac device comprising a resilient inner panel in contact with at least a portion of the heart periphery, one or more resilient members positioned about the resilient inner panel and at least partially surrounded by an expandable outer panel, wherein the resilient inner panel has a selectively inflatable end-systolic heart shape and at least one inflatable bladder with a heart shaped contoured to surround at least a portion of a heart to provide curvatures similar to the proper shape of the heart when pressurized to compress the heart during contraction without inverting or significantly perturbing the curvatures of the heart, one or more fluid connections in communication with the expandable outer panel and resilient inner panel for pressurization and depressurization;

pressurizing the direct compression cardiac device to compress the heart during contraction without inverting or significantly perturbing the curvatures of the heart; and modulating the resistance supplied by the inner panel to the heart to control the end-diastolic heart volume and remodel the heart, the resistance supplied by the expandable outer panel to the heart to control the end-systolic heart volume and remodel the heart or both.

12. The method of claim 11, wherein the one or more resilient members comprise individually a metal, an alloy, a memory metal, a composite, a polymer, a plastic or a combination thereof.

13. The method of claim 11, wherein the one or more resilient members comprise a collapsible wire frame that can be compressed for insertion and expands to a basic cup shape when inserted into a pericardial space.

14. A direct cardiac compression heart assist device comprising:

a resilient inner panel in contact with a heart periphery comprising one or more membranes having one or more resilient members and contoured to provide curvatures generally in the end-systolic shape of the heart, wherein the resilient inner panel supplies resistance to the movement of the heart to affect the end-diastolic heart volume;

an inflatable outer panel comprising one or more inflatable membranes positioned at least partially around the resilient inner panel to inflate to provide resistance to the movement of the heart and affect the end-systolic heart volume to provide curvatures similar to the proper shape of the heart when pressurized to compress the heart during contraction without inverting or significantly perturbing the curvatures of the heart, one or more fluid connections in communication with the expandable outer panel and resilient inner panel for pressurization and depressurization;

pressurizing the direct compression cardiac device to compress the heart during contraction without inverting or significantly perturbing the curvatures of the heart; and one or more fluid connections in communication with the inflatable outer panel for inflation and deflation.

15. The device of claim 14, wherein each of the one or more at least partially overlapped membranes further comprise an inflatable bladder.

16. The device of claim 15, wherein the inflatable bladder further comprises one or more active connections connectable to a source to control actively the resistance to the periphery of the heart through inflation and deflation.

17. The device of claim 14, wherein the one or more membranes comprise one or more at least partially overlapped membranes connected to form a continuous outer edge.

18. The device of claim 14, further comprising one or more mechanical compression devices for increasing the resistance applied to the heart.

19. The device of claim 14, further comprising one or more mechanical compression devices positioned about the resilient inner panel to increase the resistance applied to the heart wherein the one or more mechanical compression devices comprises a lap band or a hoop.

20. The device of claim 14, wherein the resilient inner panel, the inflatable outer panel or both comprise an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

21. The device of claim 14, wherein the one or more resilient members comprise individually a metal, an alloy, a memory metal, a composite, a polymer, a plastic or a combination thereof.

22. The device of claim 21, wherein the one or more resilient members comprise a collapsible wire frame that can be compressed for insertion and expands to a basic cup shape when inserted into a pericardial space.

23. The device of claim 14, further comprising one or more sensors, one or more electrodes to provide pacing stimuli to the heart, one or more electrodes to provide an electrical shock to the heart for defibrillation, one or more electrodes to provide an electrical stimuli to the heart, or a combination thereof in contact with the direct compression cardiac device.

24. The device of claim 14, further comprising one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

25. The device of claim 14, wherein the one or more fluid connections are connected to a gas source, a liquid source, a gel source or a combination thereof, wherein the device is inflated with positive pressure during systole and the device is deflated with suction during diastole.

26. A method of implanting a direct cardiac compression heart assist device comprising the steps of:
creating a heart apex access site;
providing a heart periphery with a direct cardiac compression heart assist device contoured to provide curvatures generally in the shape of the heart comprising a resilient inner panel comprising one or more membranes having one or more resilient members and contoured to provide curvatures generally in the shape of the heart, wherein the resilient inner panel supplies resistance to the movement of the heart to affect the end-diastolic heart volume, an inflatable outer panel comprising one or more inflatable membranes positioned at least partially around the resilient inner panel to inflate and provide resistance to the movement of the heart to affect the end-systolic heart volume and one or more fluid connections in communication with the inflatable outer panel for inflation and deflation;
providing a direct cardiac compression heart assist delivery device in communication with the heart periphery with a direct cardiac compression heart assist device to aid in the positioning about the heart;
inserting the direct cardiac compression heart assist delivery device through the heart apex access site;
positioning the direct cardiac compression heart assist device about the periphery of the heart; and
pressurizing the direct compression cardiac device to compress the heart during contraction without inverting or significantly perturbing the curvatures of the heart.

\* \* \* \* \*